US006640192B2

(12) United States Patent
Collins et al.

(10) Patent No.: US 6,640,192 B2
(45) Date of Patent: Oct. 28, 2003

(54) GENERATION OF DIVERSITY IN COMBINATORIAL LIBRARIES

(75) Inventors: John Collins, Braunschweig (DE); Peter Röttgen, Braunschweig (DE)

(73) Assignee: Cosmix Molecular Biologicals GmbH, Braunschweig (DE)

( * ) Notice: Subject to any disclaimer, the term of this patent is extended or adjusted under 35 U.S.C. 154(b) by 0 days.

(21) Appl. No.: 09/912,165

(22) Filed: Jul. 24, 2001

(65) Prior Publication Data

US 2002/0072594 A1 Jun. 13, 2002

Related U.S. Application Data

(62) Division of application No. 09/364,707, filed on Jul. 30, 1999, now Pat. No. 6,310,191, which is a continuation of application No. PCT/EP98/00533, filed on Feb. 2, 1998.

(30) Foreign Application Priority Data

Jan. 31, 1997 (EP) ............................................. 97101539

(51) Int. Cl.⁷ ........................ G01N 33/50; A61K 38/00; C07H 21/02
(52) U.S. Cl. ........................ 702/20; 530/300; 536/23.1
(58) Field of Search ................. 435/6, 320.1; 536/23.1; 530/300

(56) References Cited

FOREIGN PATENT DOCUMENTS

| | | |
|---|---|---|
| EP | 0 183 571 | 6/1986 |
| EP | 0 699 750 A1 | 3/1996 |
| WO | WO 92/06176 | 4/1992 |
| WO | WO 92/06204 | 4/1992 |
| WO | WO 95/21914 | 8/1995 |
| WO | WO 96/35781 | 11/1996 |

OTHER PUBLICATIONS

"Class–IIS Restriction Enzymes—a Review", Szybalski et al., XP–002074512, Elsevier Science Publishers, pp. 13–26, Jan. 18, 1991.

"Cloning in a Bacteriophage Lambda Vector for the Display of Binding Proteins on Filamentous Phage", Hogrefe et al., XP–002074513, Elsevier Science Publishers, pp. 85–91, Jul. 27, 1993.

Cosmix web pages, http://www.cosmix.de, last update Dec. 1, 1997, XP–002074514.

*Primary Examiner*—Kenneth R. Horlick
*Assistant Examiner*—Young Kim
(74) *Attorney, Agent, or Firm*—Marshall, Gerstein & Borun LLP

(57) ABSTRACT

The invention concerns gene banks and combinatorial derivatives thereof, prepared using phagemid- or phage-display in combination with type IIS restriction enzymes and cosmid packaging; their use for the isolation of ligands, including enzyme inhibitors, agonists and antagonists for receptors, competitive binding peptides to a defined target, diagnostic ligands for diseases and autoimmune syndromes, including surveillance tools for immune status, post-translationally modified peptides, and such ligands generated by this technology.

14 Claims, 15 Drawing Sheets

```
   1 ggcgagctcc cgtgcagcgc tccaggtacc ccgatatcag agctgaaact gttgaaagtt
  61 gtttagcaaa atcccataca gaaaattcat gaggctgtc  ctggaaagac gacaaaactt
 121 tagatcgtta cgctaactat ttcatgttc  agaataatag tgtgaatgc  tacaggcgtt gtagtttgta
 181 ctggtgacga aactcagtgt tacggtacat ggttcctat  tgggcttgct atccctgaaa
 241 atgagggtgg tggctctgag ggtgcggtt  ctgagggtgg cggttctgag ggtggcggta
 301 ctaaacctcc tgagtacggt gatacaccta ttccgggcta tacttatatc aaccctctcg
 361 acggcactta tccgcctggt actgagcaaa accccgctaa tcctaatcct tctccttgagg
 421 agtctcagcc tcttaatact ttcatgtttc agaataatag gttccgaaat aggcagggg
 481 cattaactgt ttatacgggc actgttactc aaggcactga ccccgttaaa acttattacc
 541 agtacactcc tgtatcatca aaagccatgt atgacgctta ctggaacggt aaattcagag
 601 actgcgcttt ccattctggc tttaatgaag atccattcgt ttgtgaatat caaggccaat
 661 cgtctgacct gcctcaacct cctgtcaatg ctggcggcgg ctctggtggt ggttctggtg
 721 gcggctctga gggtggtggc tctgagggtg gcggttctga gggtggcggc tctgagggag
 781 gcggttccgg tggtggctct ggttccggtg atttgattaa taaagatga tgaaagatg
       [rest partial]
```

FIGURE 6B

```
1321 gctcccttg  gagcctttt   tttggagat  tttcaacgtg  aaaaaattat  tattcgcaat
1381 tccaagctaa ttcacctcga  aagcaagctg ataaaccgat  acaattaaag  gctccttttg
1441 gagccttttt tttggagat   tttcaacgtg aaaaaattat  tattcgcaat  tccaagctct
1501 gcctcgcgcg tttcggtgat  gacggtgaaa acctctgaca  catycagctc  ccggagacgg
1561 tcacagcttg tctgtaagcg  gatgcagatc acgcgccctg  tagcggcgca  ttaagcgcgg
1621 cgggtgtggt ggttacgcgc  agcgtgaccg ctacacttgc  cagcgcccta  gcgcccgctc
1681 ctttcgcttt ctcccccttcc tttctcgcca cgttcgccag  cttccccgt   caagctctaa
1741 atcgggggct ccctttaggg  ttccgattta gtgctttacg  gcacctcgac  cccaaaaaac
1801 ttgattaggg tgatggttca  cgtagtgggc catcgcctg   atagacgtt   tttcgccctt
1861 tgacgttgga gtccacgttc  tttaatagtg gactcttgtt  ccaaactgga  acaacactca
1921 acctatctc  ggtctattct  tttgatttat aagggattt   gccgatttcg  gcctattggt
1981 taaaaatga  gctgatttaa  caaaaattta acgcgaattt  taacaaaata  ttaacgttta
2041 caatttgatc tgcgctcggt  cgttcggctg cggcgagcgg  tatcagctca  ctcaaaggcg
2101 gtaatacggt tatccacaga  atcaggggat aacgcaggaa  agaacatgtg  agcaaaaggc
2161 cagcaaaagg ccaggaaccg  taaaaaggcc gcgttgctgg  cgtttttcca  taggctccgc
2221 cccctgacg  agcatcacaa  aaatcgacgc tcaagtcaga  ggtggcgaaa  cccgacagga
2281 ctataaagat accaggcgtt  tccccctgga agctccctcg  tgcgctctcc  tgttccgacc
2341 ctgccgctta ccggatacct  gtccgccttt ctcccttcgg  gaagcgtggc  gctttctcaa
2401 tgctcacgct gtaggtatct  cagttcggtg taggtcgttc  gctccaagct  gggctgtgtg
2461 cacgaacccc ccgttcagcc  cgaccgctgc gccttatccg  gtaactatcg  tcttgagtcc
2521 aacccggtaa gacacgactt  atcgccactg gcagcagcca  ctggtaacag  gattagcaga
2581 gcgaggtatg taggcggtgc  tacagagttc ttgaagtggt  ggcctaacta  cggctacact
```

FIGURE 6C

```
2641  agaaggacag tatttggtat ctgcgctctg ctgaagccag ttaccttcgg aaaaagagtt
2701  ggtagctctt gatccggcaa acaaaccacc gctggtagcg gtggtttttt tgtttgcaag
2761  cagcagatta cgcgcagaaa aaaaggatct caagaagatc ctttgatctt tctacgggg
2821  tctgacgctc agtggaacga aaactcacgt taagggattt tggtcatgag attatcaaaa
2881  aggatcttca cctagatcct tttaaattaa aaatgaagtt ttaaatcaat ctaaagtata
2941  tatgagtaaa cttggtctga cagttaccaa tgcttaatca gtgaggcacc tatcctcagcg
3001  atctgtctat ttcgttcatc catagttgcc tgactccccg tcgtgtagat aactacgata
3061  cgggagggct taccatctgg ccccagtgct gcaatgatac gccgagaccc acgctcaccg
3121  gctccgcttt tatcagcaat aaaccagcca gccggaaggg cccgagcgcag aagtggtcct
3181  gcaactttat ccgcctccat ccagtctatt aattgttgcc gggaagctag agtaagtagt
3241  tcgccagtta atagtttgcg caacgttgtt gccattgctg caggcatcgt ggtgtcacgc
3301  tcgtcgtttg gtatggcttc attcagctcc ggttcccaac gatcaaggcg agttacatga
3361  tcccccatgt tgtgcaaaaa agcggttagc tccttcggtc ctccgatcgt tgtcagaagt
3421  aagttggccg cagtgttatc actcatggtt atggcagcac tgcataattc tcttactgtc
3481  atgccatccg taagatgctt ttctgtgact ggtgagtact caaccaagtc atcctgagaa
```

FIGURE 6D

```
3541  tagtgtatgc ggcgaccgag ttgctcttgc ccggcgtcaa cacggataa taccgcgcca
3601  catagcagaa ctttaaaagt gctcatcatt ggaaaaacgtt cttcggggcg aaaactctca
3661  aggatcttac cgctgttgag atccagttcg atgtaaccca ctcgtgcacc caactgatct
3721  tcagcatctt ttactttcac cagcgtttct gggtgagcac aaacaggaag gcaaaatgcc
3781  gcaaaaaagg gaataagggc gacacggaaa tgttgaatac tcatactctt cctttttcaa
3841  tattattgaa gcagacagtt ttattgttca tgatgatata tttttatctt gtgcaatgta
3901  acatcagaga tttgagaca caacagatct ggccatcatg atggaatgtt tccccggtgg
3961  tgttatctgg cagcagtgcc gtcgatagta tgcaattgat aattattatc atttgcgggt
4021  cctttccggc gatccgccttt gttacggggc ggcgaccctg cgggttttcg ctatttatga
4081  aaattttccg gttaaggcg tttccgttct tcttcgtcat aacttaatgt ttttatttaa
4141  aatacccctct gaaaagaaag agaggatctc tcacctacca gtgctgaaag cgagctttt ggccacgatg
4201  cgtccggcgt agaggatctc tcacctacca gtgctgaaag cgagctttt ggccacgatg
4261  tataaaaac atacagataa ccatctgcgg tgataaatta aataaattca
4321  aataccactg gcggtgatac agcaggacgc tctctggcgg tgttgacata
4381  cgctcttaaa attaagccct gaagaagggc actgaccacc atgaaggtga
4441  tgatacgaaa cgaagcattg gaattctaca agcagaaggct ttggggtgtg
4501  atttcagtg tcagaagtcg accaaggagg tctagataac agaagcagca
4561  acagctatcg cgattgcagt ggcactggct ggtttcgcta ccgtagcgca aatgaaaaag
       ccgtagcgca ggcc
```

FIGURE 6E

```
   1  ggcgagctcc  cgtgcagcgg  tcttcagcgc  ttgccgtctg  accgtagcgc  tggaagacgc
  61  tccagagggt  acccgatat   cagagctgaa  actgttgaaa  gttgtttagc  aaaatcccat
 121  acagaaaatt  catttactaa  cgtctggaaa  gacgacaaaa  ctttagatcg  ttacgctaac
 181  tatgagggct  gtctgtgaa   tgctacaggc  gttgtagttt  gtactggtga  cgaaactcag
 241  tgttacggta  catgggttcc  tattggctt   gctatccctg  aaaatgaggg  tggtggctct
 301  gagggtggcg  gttctgaggg  tggcggttct  gagggtggcg  gtactaaacc  tcctgagtac
 361  ggtgatacac  ctattccggg  ctatactat   gtactaaccc  tcgacggcac  ttatccgcct
 421  ggtactgagc  aaaaccccgc  taatcctaat  atcaaccctc  aggagtctca  gcctcttaat
 481  actttcatgt  ttcagaataa  taggttccga  cctttcttg   gggcattaac  tgtttatacg
 541  ggcactgtta  ctcaaggcac  tgacccccgtt  aataggcagg  accagtacac  tcctgtatca
 601  tcaaaagcca  tgtatgacgc  ttactggaac  aaaacttatt  gagactgcgc  tttccattct
 661  ggctttaatg  aagatccatt  cgttgtgaa   tatcaaggcc  aatcgtctga  cctgcctcaa
 721  cctcctgtca  atgctggcgg  cggctctggt  ggtggttctg  gtggcggctc  tgaggtggt
 781  ggctctgagg  gtggcggttc  tgaggtggcgg  ggctctgagg  gaggcggttc  cggtgtggcg
 841  tctggttccg  gtgattttga  ttatgaaaag  atggcaaacg  ctaataaggg  ggctatgacc
 901  gaaaatgccg  atgaaaacgc  gctacagtct  gacgctaaag  gcaaacttga  ttctgtcgct
 961  actgattacg  gtgctgctat  cgatggtttc  attggtgacg  tttccggcct  tgctaatggt
1021  aatggtgcta  ctggtgattt  tgctggctct  aattccccaa  tggctcaagt  cggtgacggt
1081  gataattcac  ctttaatgaa  taatttccgt  caatatttac  cttccctccc  tcaatcggtt
1141  gaatgtcgcc  cttttgtctt  tggcgctggt  aaaccatatg  aatttctat   tgattgtgac
1201  aaaataaact  tattccgtgg  tgtctttgcg  tttcttttat  atgttgccac  ctttatgtat
```

FIGURE 7B

```
1261  gtattttcta  cgtttgctaa  catactgcgt  aataaggagt  cttaatgact  ctagaggtcg
1321  aaattcacct  cgaaagcaag  ctgataaacc  gatacaatta  aggctcctt   ttggagcctt
1381  tttttttgga  gattttcaac  gtgaaaaaat  tattattcgc  aattccaagc  taattcacct
1441  cgaaagcaag  ctgataaacc  gatacaatta  aggctcctt   ttggagcctt  ttttttga
1501  gatttcaac   gtgaaaaaat  tattattcgc  aattccaagc  tctgcctcgc  gcgtttcggt
1561  gatgacggtg  aaaacctctg  acacatgcag  ctcccggaga  tctgcctcgc  ttgtctgtaa
1621  gcggatgcag  atcacgcgcc  ctgtagcggc  gcattaagcg  cggcgggtgt  ggtggttacg
1681  cgcagcgtga  ccgctacact  tgccagcgcc  ctagcgcccg  ctcctttcgc  tttcttccct
1741  tcctttctcg  ccacgttcgc  cagctttccc  cgtcaagctc  taaatcgggg  gctcctta
1801  gggttccgat  ttagtgcttt  acggcacctc  gaccccaaaa  aacttgatta  gggtgatggt
1861  tcacgtagtg  ggccatcgcc  ctgatagacg  gtttttcgcc  ctttgacgtt  ggagtccacg
1921  ttctttaata  gtggactctt  gttccaaact  ggaacaacac  tcaaccctat  ctcggtctat
1981  tcttttgatt  tataagggat  tttgccgatt  tcggcctatt  ggttaaaaaa  tgagctgatt
2041  taacaaaaat  ttaacgcgaa  ttttaacaaa  atattaacgt  ttacaatttg  atctgcgctc
2101  ggtcgttcgg  ctgcgggcgag  cggtatcagc  tcactcaaag  gcggtaatac  ggttatccac
2161  agaatcaggg  gataacgcag  gaaagaacat  gtgagcaaaa  ggccagcaaa  aggccaggaa
2221  ccgtaaaaag  gccgcgttgc  tggcgttttt  ccataggctc  cgcccccctg  acgagcatca
2281  caaaaatcga  cgctcaagtc  agaggtggcg  aaacccgaca  ggactataaa  gataccaggc
2341  gtttccccct  ggaagctccc  tcgtgcgctc  tcctgttccg  accctgccgc  ttaccggata
2401  cctgtccgcc  tttctccctt  cgggaagcgt  ggcgctttct  caatgctcac  gctgtaggta
2461  tctcagttcg  gtgtaggtcg  ttcgctccaa  gctgggctgt  gtgcacgaac  ccccgttca
```

FIGURE 7C

```
2521  gcccgaccgc  tgcgccttat  ccggtaacta  tcgtcttgag  tccaacccgg  taagacacga
2581  cttatcgcca  ctggcagcag  ccactggtaa  caggattagc  agagcgaggt  atgtaggcgg
2641  tgctacagag  ttcttgaagt  ggtggcctaa  ctacggctac  actagaagga  cagtatttgg
2701  tatctgcgct  ctgctgaagc  cagttacctt  cggaaaaaga  gttggtagct  cttgatccgg
2761  caaacaaacc  accgctggta  gcggtggttt  tttgttttgc  aagcagcaga  ttacgcgcag
2821  aaaaaaagga  tctcaagaag  atcctttgat  cttcctacg  gggtctgacg  ctcagtggaa
2881  cgaaaactca  cgttaaggga  tttggtcat  gagattatca  aaaggatct  tcacctagat
2941  ccttttaaat  taaaaatgaa  gttttaaatc  aatctaaagt  atatatgagt  aaacttggtc
3001  tgacgttac  caatgcttaa  tcagtgaggc  acctatctca  gcgatctgtc  tatttcgttc
3061  atccatagtt  gcctgactcc  ccgtcgtgta  gataactacg  atacgggagg  gcttaccatc
3121  tggccccagt  gctgcaatga  taccgcgaga  cccacgctca  ccggctccgc  ttttatcagc
3181  aataaaccag  ccagccggaa  gggccgagcg  cagaagtggt  cctgcaactt  tatccgcctc
3241  catccagtct  attaattgtt  gccgggaagc  tagagtaagt  agttcgccag  ttaatagttt
3301  gcgcaacgtt  gttgccattg  ctgcaggcat  cgtggtgtca  cgctcgtcgt  ttggtatggc
3361  ttcattcagc  tccggttccc  aacgatcaag  gcgagttaca  tgatccccca  tgttgtgcaa
3421  aaaagcggtt  agctccttcg  gtcctccgat  cgttgtcaga  agtaagttgg  ccgcagtgtt
3481  atcactcatg  gttatggcag  cactgcataa  ttctcttact  gtcatgccat  ccgtaagatg
```

FIGURE 7D

```
3541  cttttctgtg  actggtgagt  actcaaccaa  gtcattctga  gaatagtgta  tgcggcgacc
3601  gagttgctct  tgcccggcgt  caacacggga  taatacgcg   ccacatagca  gaactttaaa
3661  agtgctcatc  attgaaaaac  gttcttcggg  gcgaaaactc  tcaaggatct  taccgctgtt
3721  gagatccagt  tcgatgtaac  ccactcgtgc  acccaactga  tcttcagcat  cttttacttt
3781  caccagcgtt  tctgggtgag  caaaaacagg  aaggcaaaat  gccgcaaaaa  agggaataag
3841  ggcgacacgg  aaatgttgaa  tactcatact  cttcctttt   caatattatt  gaagcagaca
3901  gttttattgt  tcatgatgat  atatttttat  cttgtgcaat  gtaacatcag  agattttgag
3961  acacaacaga  tctggccatc  atgatgaat   gtttcccccgg tggtgttatc  tggcagcagt
4021  gccgtcgata  gtatgcaatt  atcatttgcg  ggtcccttcc  ggcgatccgc
4081  cttgtttacgg ggcggcgacc  tcgcgggttt  tcgctattta  tgaaaatttt  ccggtttaag
4141  gcgtttccgt  tcttcttcgt  cataacttaa  tgttttattt  taaaataccc  tctgaaaaga
4201  aaggaaacga  caggtgctga  aagcgagctt  tttggccacg  atgcgtccgg  cgtagaggat
4261  ctctcaccta  ccaaacaatg  ccccccctgca aaaataaat   tcatataaaa  aacatacaga
4321  taaccatctg  cggtgataaa  ttatctctgg  cggtgttgac  ataaatacca  ctggcggtga
4381  tactgagcac  atcagcagga  cgcactgacc  accatgaagg  tgacgctctt  aaaattaagc
4441  cctgaagaag  ggcagcattc  aaagcagaag  gctttgggt   gtgtgatacg  aaacgaagca
4501  ttggaattct  acaacttgct  tggattccta  caaagaagca  gcaattttca  gtgtcagaag
4561  tcgaccaagg  agtctagat   aacgagggca  aaaaatgaaa  aagacagcta  tcgcgattgc
4621  agtggcactg  gctggtttcg  ctaccgtagc  gcaggcc
```

FIGURE 7E

GENERATION OF DIVERSITY IN COMBINATORIAL LIBRARIES

The present application is a divisional application of U.S. application Ser. No. 09/364,707, which was filed Jul. 30, 1999 and issued as U.S. Pat. No. 6,310,191, which in turn was a continuation of PCT/EP98/00533, and was filed Feb. 2, 1998 and claimed priority to EP 97 101 539 which was filed Jan. 31, 1997.

Biotech evolutionary methods, including combinatorial libraries and phage-display technology (PARMLEY & SMITH 1988; SCOTT & SMITH 1990; SMITH 1993), are used in the search for novel ligands of diagnostic, biomedical and pharmaceutical use (reviews; CORTESE 1996; COLLINS 1997). These methods, which use empirical procedures to select molecules with required characteristics, e.g. binding properties, from large populations of variant gene products has been compared to the process of natural evolution. Evolution includes the generation of mutation, selection of functionality over a time period and the ability of the systems to self-replicate. In particular natural systems use recombination to reassort mutations accumulated in the selected population to exponentially increase the combinations of mutations and thus increase the number of variants in the population. This latter aspect, namely the introduction of recombination within mutant genes has only recently been applied to biotech evolutionary methods, although it has been used to increase the size of initial phage-display libraries (e.g. WATERHOUSE 1993; TSURUSHITA 1996; SODOYER 1994; FISCH 1996). STEMMER 1994a, 1994b and 1995 teach that recombination amongst a population of DNA molecules can be achieved in vitro by PCR amplification of a mixture of small overlapping fragments with (1994a, 1994b) or without (STEMMER 1995) primer oligonucleotide sequences being used to drive the PCR reaction. The method is not applicable to recombination within a fully randomized (highly mutated) sequence since the method relies on high homology of the overlapping sequences at the site of recombination. STEMMER 1994b and CRAMERI 1996a do, however, demonstrate the usefulness of in vitro recombination for molecular evolution, where CRAMERI 1996b also demonstrate the use of the method in conjunction with phage-display, even though their method is confined to regions of low mutant density (ca. 0.5–1% of the bases are mutated in their method) as they state "the advantages of recombination over existing mutagenesis methods are likely to increase with the numbers of cycles of molecular evolution" (STEMMER 1994b). We point out that this is due to the self-evident fact that the number of variants created by mutagenesis introducing base changes in existing mutant structures is an additive i.e., a linearly increasing function, whereas the use of recombination between mutated variants yields novel variants as an exponential function of the initial number of variants. The classical phage-display libraries are thus at a grave disadvantage for the generation of novel variants; e.g. to encompass all the possible variants of an octapeptide sequence $20^8=2.56 \times 10^{10}$ different variants would be required.

MARKS 1992 state the importance of recombination in the generation of higher specificity in combinatorial libraries e.g. in attaining antibodies of higher specificity and binding constants in the form of reshuffling light and heavy chains of immunoglobulins displayed in phage-display libraries. These authors do not instruct how the shuffling of all the light and heavy chains in a population heterogeneous in. both chains can be achieved, e.g. by a vector allowing recombination. Heavy and light chains were selected one after the other, i.e. an optimal heavy chain first selected from a heterogeneous heavy chain population in the presence of a constant light chain, then by preparing a new library, an optimal light chain in combination with the preselected optimal heavy chain. The extensive time consuming sequential optimization strategies currently utilized including consensus-mutational libraries, in vivo mutagenesis, error-pone PCR as well as chain shuffling are summarized in FIGS. 5 and 6 of COLLINS 1997.

General Background to Phase and Phape-display Libraries

Gene libraries are generated containing extremely large number ($10^6$ to $10^{10}$) of variants. The variant gene segments are fused to a coat protein gene of a filamentous bacteriophage (e.g. M13, fd or fl), and the fusion gene is inserted into the genome of the phage or of a phagemid. A phagemid is defined as a plasmid containing the packaging and replication origin of the filamentous bacteriophage. This latter property allows the packaging of the phagemid genome into a phage coat when it is present in an *Escherichia coli* host strain infected with a filamentous phage (superinfection). The packaged particles produced, be they phage or phagemid, display the fusion protein on the surface of the particles secreted into the medium. Such packaged particles are able to inject their genomes into a new host bacterium, where they can be propagated as phage or plasmids, respectively. The special property of the system lies in the fact that since the packaging takes place in individual cells usually infected by a single variant phage/phagemid, the particles produced on propogation contain the gene encoding the particular variant displayed on the particle's surface. Several cycles of affinity selection for clones exhibiting the required properties due to the particular property of the variant protein displayed, e.g. binding to a particular target molecule immobilized on a surface, followed by amplification of the enriched clones leads to the isolation of a small number of different clones having these properties. The primary structure of these variants can then be rapidly elucidated by sequencing the hypermutated segment of the variant gene.

Efficiency of Producing Combinatorial Libraries

There are a number of factors which limit the potential of this technology. The first is the number and diversity of the variants which can be generated in the primary library. Most libraries have been generated by transformation of ligated DNA preparations into *Escherichia coli* by electroporation. This gives an efficiency of ca. 0.1 to 1×106 recombinants/microgram ligated phage DNA. The highest cloning efficiency reported (of 107 recombinants per microgram insert DNA) is obtained using special lambda vectors into which a single filamentous phage vector is inserted, in a special cloning site, bracketted by a duplication of the filamentous phage replication/packaging origin (AMBERG 1993; HOGREFE 1993a+b). The DNA construct is efficiently introduced into the *Escherichia coli* host after packaging into a lambda bacteriophage coat in an in vitro lambda packaging mix. Infection of a strain carrying such a hybrid phagemid by an M13-helper phage allows excision and secretion of the insert packed in a filamentous phage coat. Neither AMBERG 1993 nor HOGREFE 1993a+b instruct on how the method may be used to introduce recombination during this procedure. Although they mention that the efficiency may be improved by the use of type IIS restriction endonucleases during the construction of the concatemers used as substrate for the in vitro packaging no examples are given and in the ensuing five years no examples have appeared in the literature. The procedure described in our invention also uses the high efficiency of the in vitro lambda packaging, but maximizes the capacity of the cloning vector by using a cosmid vector (8) in which many copies (say 8) of the phagemid are inserted in each construct. One of the surprising innovative aspects of this procedure is the discovery of a number of protocols for the de novo synthesis of large hypervariable libraries. One type is particularly efficient, in that phagemid/cosmid vectors are forced to integrate into the hybrid concatamers oriented in the same orientation. Any variant of the protocol which does not ensure this feature does not work efficiently.

The Use of Type IIS Restriction Endonucleases

SZYBALSKI 1991 teaches a large number of novel applications for type IIS restriction endonucleases, including precise trimming of DNA, retrieval of cloned DNA, gene assembly, use as a universal restriction enzyme, cleavage of single-stranded DNA, detection of point mutations, tandem amplification, printing amplification reactions and localization of methylated bases. They do not give any instruction as to how such enzymes can be used in the creation of recombination within highly mutated regions, e.g. within a combinatorial library.

Reference List

Amberg, J, Hogrefe, H., Lovejoy, H., Hay, B., Shopes, B, Mullinax, R. and Sorge, J. A. (1993), Strategies, 5, 2–3.

Collins, J. (1997) Phage display. In Moos, W. H. et al. (eds) Annual reports in combinatorial chemistry and molecular diversity. Vol. 1., ESCOM Science publ., Leiden. pp. 210–262.

Cortese, R. (ed.) (1996) Combinatorial libraries: Synthesis, Screening and Application potential. Walter de Gruyter, Berlin.

Crameri, A., Whitehom, E. A., Tate, E. and Stemmer, W. P. C. (1996a) 14, 315–319.

Crameri, A., Cwirla, S. and Stemmer, W. P. C. (1996b) Nat. Med. 2, pg. 100.

Fisch, I., Kontermann, R. E., Finnern, R., Hartley, O., Soler-Gonzalez, A. S., Griffiths, A. D. and Winter, G. (1996) Proc. Natn. Acad. Sci. USA. 93, 7761.

Marks, J. D.; Griffiths, A. D.; Malmqvist, M.; Clackson, T. P.; Bye, J. M. and Winter, G. (1992) BioTechnol. 10, 779–783.

Hogrefe, H. H., Amberg, J. R., Hay, B. N., Sorge, J. A. and Shopes, B. (1993) Gene, 137, 85–91.

Hogrefe, H. H., Mullinax, R. L., Lovejoy, A. E., Hay, B. N. and Sorge, J. A. (1993) Gene 128, 119–126.

Parmley, S. F. and Smith, G. P. (1988) Gene 73, 305–318.

Scott, J. K. and Smith, G. P. (1990) Science 249, 386–390.

Smith, G. P. (1993) Gene 128, 1–2.

Sodoyer, R., Aujume, L., Geoffrey, F., Pion, C., Puebez, I., Montegue, B., Jacquemot, P. and Dubayle, J. (1996) In Kay, B. K. et al. (eds.) Phage display of peptides and proteins. A laboratory manual. Academic Press, San Diego. Pp. 215–226.

Stemmer, W. P. C. (1994a) Nature (Lond.) 370, 389–391.

Stemmer, W. P. C. (1994b) Proc. Nat. Acad. Sci. USA, 91, 10747–10751.

Stemmer, W. P. C. (1995) Gene 164, 49–53.

Szybalski, W., Kim, S. C., Hasan, N. and Podhajska, A. J. (1991) Gene, 100, 13–26.

Tsurushita, M., Fu, H. and Warren, C. (1996) Gene, 172, 59.

Waterhouse, P., Griffiths, A. D., Johnson, K. S. and Winter, G. (1993a) Nucleic Acid Res. 2265–2269.

According to a first embodiment the invention concerns a bank of genes, wherein said genes comprise a double stranded DNA sequence which is represented by the following formula of one of their strands:

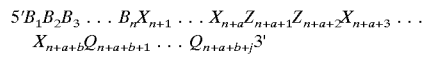

wherein n, a, b and j are integers and n>3, a>1, b>3 and j>1, wherein $X_{n+1} \ldots X_{n+a+b}$ is a hypervariable sequence and B, X, Z and Q represent adenine (A), cytosine (C), guanine (G) or thymine (T), (i) Z represents G or T at a G:T ratio of about 1:1, and/or (ii) Z represents C or T at a C:T ratio of about 1:1, and/or (iii) Z represents A or G at a A:G ratio of about 1:1, and/or (iv) Z represents A or C at a A:C ratio of about 1:1, and wherein subsequences $B_1 \ldots B_n$ and/or $Q_{n+a+b+1} \ldots Q_{n+a+b+j}$ represent recognition sites for restriction enzymes, and wherein the recognition sites are oriented such that their cleavage site upon cleavage generates a cohesive end including the two bases designated Z.

Restriction of this sequence with a type IIS restriction enzyme as thus described, followed by religation leads to the recombination of the hypervariable regions located 5' and 3' of the cleavage site. This is the essence of the methodology which we designate "cosmix-plexing". It is essential in this procedure that the fragments generated on cleavage by the restriction enzyme are religated in the correct orientation ("head-to-tail"), whereby the Z sequences are chosen for the four libraries ((i) to (iv)) so as to ensure this (see below) yet still allowing all possible amino-acids to be encoded at the cleavage site. If this correct orientation is not ensured there will be a drastic reduction in both the percent of correctly reconstituted fusion-protein genes, a reduction in the proportion of molecules which can be packaged in vitro in the lambda-packaging extracts (which requires the correct orientation of the cos-sites), as well as a reduction in the proportion of in vivo excisable phagemid copies from the cosmid concatemer (excision requires the correct orientation of consecutive phage replication origins).

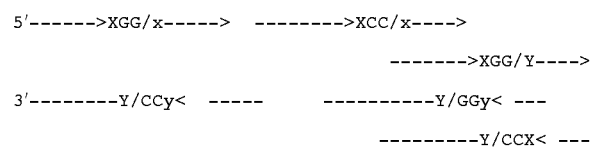

To prevent the problems arising from false orientation (head-to-head) mentioned in the previous paragraph, the four gene libraries mentioned in claim must be kept separated during cosmix-plexing. In fact with respect to the formation of recombinants the libraries behave as 16 separate sets which cannot recombine with each other:four libraries maintained separately, where each set contains four possible cohesive ends, e.g. library (i) with Z=G or T contains:

```
5'---->XGT/Y---->,      ----->XGG/Y----->,
            ---->XTG/Y---->,  and  ---->XTT/Y----->
3'------>y/CA x< --   ------->y/CC x< -----
            -----y/AC x< ----   ------y/AA x< ----
```

It is evident that problems of false orientation will arise on mixing the different libraries, e.g.

The AC library (iv) will contain AA, AC, CA and CC sequences which can pair in the false orientation with, respectively each of the cohesive ends generated in library (i).

A specific embodiment of the invention concerns a bank of genes wherein subsequences $B_1 \ldots B_n$ or $Q_{n+a+b+1} \ldots Q_{n+a+b+j}$ represent recognition sites for restriction enzymes and wherein the recognition sites are orientated such that their cleavage site upon cleavage generates a cohesive end including the two bases designated Z.

Further, a specific embodiment concerns a bank of genes, wherein the cohesive end is a 2 bp single strand end formed by the two bases designated Z.

Further, a specific embodiment concerns a bank of genes wherein each gene is provided as display vector, especially as M13 phage or M13-like phage or as phagemid.

Another embodiment of the invention concerns a set of four gene banks according to the invention wherein the gene banks are characterized as follows:

first gene bank: Z represents G or T, preferentially at a G:T ratio of about 1:1;
second gene bank: Z represents C or T, preferentially at a C:T ratio of about 1:1;
third gene bank: Z represents A or G, preferentially at a A:G ratio of about 1:1; and
fourth gene bank: Z represents A or C, preferentially at a A:C ratio of about 1:1.

A specific embodiment of the invention concerns a set of four gene banks wherein each gene is provided as display vector, especially as M13 phage or M13-like phage or as phagemid.

Another embodiment of the invention concerns a bank of genes wherein said genes comprise a double stranded DNA sequence which is represented by the following formula of one of their strands:

$$5'B_1B_2B_3 \ldots B_nX_{n+1} \ldots X_{n+a}Z_{n+a+1}Z_{n+a+2}X_{n+a+3} \ldots X_{n+a+b}Q_{n+a+b+1} \ldots Q_{n+a+b+j}3'$$

wherein n, a, b and j are integers and
n>3, a>1, b>3 and i>1,
wherein $X_{n+1} \ldots X_{n+a+b}$ is a hypervariable sequence and B, X, Z and Q represent adenine (A), cytosine (C), guanine (G) or thymine (T), and wherein
four sets of oligonucleotide sequences comprising $Z_{n+a+1}$ and $Z_{n+a+2}$ are present, preferentially at a ratio of (i):(ii):(iv) of about 1:1:2:2, wherein the four sets are characterized as follows:
first set: $Z_{n+a+1}$ represents G and $Z_{n+a+2}$ also represents G;
second set: $Z_{n+a+1}$ represents C and $Z_{n+a+2}$ represents T;
third set: $Z_{n+a+1}$ represents A and $Z_{n+a+2}$ represents A or C, preferentially at A:C ratio of about 1:1; and
fourth set: $Z_{n+a+1}$ represents T and $Z_{n+a+2}$ represents C or G. preferentially at a C:G ratio of about 1:1, and wherein sequences $B_1 \ldots B_n$ and/or $Q_{n+a+b+1} Q_{n+a+b+j}$ represent recognition sites for restriction enzymes, wherein the recognition sites are orientated such that their cleavage site upon cleavage generates a cohesive end including the two bases designated Z.

A specific embodiment of the invention concerns a bank of genes wherein the four sets of oligonucleotide sequences are present at a ratio of (i):(ii):(iii):(iv) of (0 to 1):(0 to 1):(0 to 1):(0 to 1) with the proviso that at least one of said sets is present.

Further, a specific embodiment of the invention concerns a bank of genes wherein subsequences $B_1 \ldots B_n$ and/or $Q_{n+a+b+1} \ldots Q_{n+a+b+j}$ represent recognition sites for restriction enzymes and wherein the recognition sites are orientated such that their cleavage site upon cleavage generates a cohesive end including the two bases designated Z.

Further, a specific embodiment of the invention concerns a bank of genes wherein the cohesive end is a 2 bp single strand end formed by the two bases designated Z.

Another embodiment of the invention concerns bank of genes wherein said genes comprise a double stranded DNA sequence which is represented by the following formula of one of their strands:

$$5'B_1B_2B_3 \ldots B_nX_{n+1} \ldots X_{n+a}Z_{n+a+1}Z_{n+a+2}X_{n+a+3} \ldots X_{n+a+b}Q_{n+a+b+1} \ldots Q_{n+a+b+j}3'$$

wherein n, a, b and j are integers and
n>3, a>1, b>3 and j>1,
wherein $X_{n+1} \ldots X_{n+a+b}$ is a hypervariable sequence and B, X, Z and Q represent adenine (A), cytosine (C), guanine (G) or thymine (T), and wherein
the following six sets of oligonucleotide sequences comprising $X_{n+a}$, $Z_{n+a+1}$ and $Z_{n+a+2}$ are present, preferably at a ratio of (i):(ii):(iii):(iv):(v):(vi) of about 3:4:3:4:4:1, wherein the six sets are characterized as follows:
first set: $X_{n+a}$ represents A, G and/or T, preferentially at a ratio of about 1:1:1 or $X_{n+a}$ represents C, G and/or T, preferentially at a ratio of about 1:1:1, $Z_{n+a+1}$ represents G and $Z_{n+a+2}$ represents G;
second set: $X_{n+a}$ represents A, C, G and/or T, preferentially at a ratio of about 1:1:1:1, $Z_{n+a+1}$ represents C and $Z_{n+a+2}$ represents T;
third set: $X_{n+a}$ represents A, C and/or G, preferentially at a ratio of about 1:1:1, $Z_{n+a+1}$ represents A and $Z_{n+a+2}$ represents A;
fourth set: $X_{n+a}$ represents A, C, G and/or T, preferentially at a ratio of about 1:1:1:1, $Z_{n+a+1}$ represents A and $Z_{n+a+2}$ represents C;
fifth set: $X_{n+a}$ represents A, C, G and/or T, preferentially at a ratio of about 1:1:1:1, $Z_{n+a+1}$ represents T and $Z_{n+a+2}$ represents C;
sixth set: $X_{n+a}$ represents A, $Z_{n+a+1}$ represents T and $Z_{n+a+2}$ represents G.

"Single-tube" Method

Problem

A method should be developed which allows cosmixplexing without maintaining separate libraries. This would have the advantage of reducing manipulation, involved in screening the four separate libraries, as previously described. This would offer a saving in both time and materials. This has been achieved in two separate versions of the invention.

Solution

It is possible to select combinations of nucleotides within the cohesive ends generated by type IIS restriction within the aforementioned sequence, i.e. ZZ, in which all the clones are present in a single library and in which the possibility of false orientation during ligation, and the associated loss of efficiency associated with this, is eliminated. At the same time the number of subsets, defined by the number of different cohesive ends which can be generated, which cannot interact (recombine) with each other, is reduced from the 16 sets, as in the previously described version of the method, to 6.

Designing the Sequences

The combinations of 2 bp single-strand cohesive end sequences which can be generated at ZZ are theoretically as follows:

| AA | CA | GA | TA |
|----|----|----|----|
| AC | CC | GC | TC |
| AG | CG | GG | TG |
| AT | CT | GT | TT |

Of these, the sequences with an inverted symmetry axis (palindromes: AT, TA, GC, CG), can pair in both orientations and are thus to be eliminated from cosmix-plexing libraries for the reasons given above. The remaining 12 sequences are actually 6 sets of complementary pairs (e.g. CC+GG, AA+TT, CA+TG). By choosing one partner from each pair (total of 6) a single set of cohesive ends can be generated which can pair only in the correct "head-to-tail" orientation. The actual choice of sequences takes the codon usage into account, assuming that ZZ are chosen as the 2nd and 3rd position of the codon. Determining are the aminoacids which are encoded by either a single or only two codons (single codon methionine (TG) and tryptophan (GG); after elimination of the palindromic sequences there also only single codons available encoding aspartic acid (Asp), asparagine (Asn), cystine (Cys), histidine (His) and tyrosine (Tyr). To encode Asp, Asn, His and Tyr an AC sequence is required. Selecting AC has the default that the complimentary sequence GT must be avoided. This is the only possibility of encoding Cys. However, the inclusion of Cys within the hypervariable sequence often causes problems of misfolding and the formation of dimeric aggregates, dependent on the redox potential of the environment. It was thus decided to create a set in which Cys codons are eliminated, but which will be of great use in many applications, including cyclic peptide library formation. If the sequence AA is chosen to encode glutamic acid (Glu), glutamine (Gln) and lysine (Lys) also allowing the stop-codon TAA, then TT must be eliminated. The consequence of this is that TC must also be included so that phenylalanine (Phe) and isoleucine (Ile) can be encoded. The elimination of the complimentary GA is without consequence since other GG codon(s) encode argenine (Arg) and glycine (Gly). The elimination of CC is then without consequence, since alanine (Ala), proline (Pro), serine (Ser) and threonine (Thr) can be encoded by CT-containing codons. This is the argumentation for the selection of ZZ sequences designated "combination A" below.

For the sake of completeness:if the doublet AA were left out and, consequently TT included, then AG must be included to encode Glu, Gln and Lys. In order to encode Ala and Pro, either CT (combination B) or CA (combination C) must now be included. This leads to the inclusion of either AG and CT (combi. B), or CA and TG (combi. C) as complimentary pairs. Combinations B and C thus do not represent an adequate solution to the problem.

| combination A | | combination B | | combination C | |
|---|---|---|---|---|---|
| AA | TT | AA | TT | AA | TT |
| AC | GT | AC | GT | AC | GT |
| AG | CT | AG | CT | AG | CT |
| CA | TG | CA | TG | CA | TG |
| CC | GG | CC | GG | CC | GG |
| GA | TC | GA | TC | GA | TC |

Sequences chosen are shown in bold type. Complementary pairs are adjacent to each other.

TABLE 1

Genetic code; the selection of XZZ codons used according to combination A is shown in bold type.

| Ala | Arg | Asp | Asn | Cys | Glu | Gln | Gly | His | Ile | Leu |
|---|---|---|---|---|---|---|---|---|---|---|
| GCA | AGA | GAC | AAC | TGC | GAA | CAA | GGA | CAC | ATA | TTA |
| GCC | AGG | GAT | AAT | TGT | GAG | CAG | GGC | CAT | ATC | TTG |
| GCG | CGA | | | | | | GGG | | ATT | CTA |
| GCT | CGC | | | | | | GGT | | | CTC |
| | CGG | | | | | | | | | CTG |
| | CGT | | | | | | | | | CTT |

| Lys | Met | Phe | Pro | Ser | Thr | Trp | Tyr | Val | Stop |
|---|---|---|---|---|---|---|---|---|---|
| AAA | ATG | TTC | CCA | AGC | ACA | TGG | TAC | GTA | TAA |
| AAG | | TTT | CCC | AGT | ACC | | TAT | GTC | TAG |
| | | | CCG | TCA | ACG | | | GTG | TGA |
| | | | CCT | TCC | ACT | | | GTT | |
| | | | | TCG | | | | | |
| | | | | TCT | | | | | |

TABLE 2

Frequency of the amino-acids, comparing the selected combination A (above) and the natural frequency of all codons.

| Amino-acid | natural frequency | Combination A |
|---|---|---|
| Ala | 4 | 1 |
| Arg | 6 | 2 |
| Asp | 2 | 1 |
| Asn | 2 | 1 |
| Cys | 2 | 0 |
| Glu | 2 | 1 |
| Gln | 2 | 1 |
| Gly | 4 | 1 |
| His | 2 | 1 |
| Ile | 3 | 1 |
| Leu | 6 | 3 |
| Lys | 2 | 1 |
| Met | 1 | 1 |
| Phe | 2 | 1 |
| Pro | 4 | 1 |
| Ser | 6 | 1 |
| Thr | 4 | 1 |

TABLE 2-continued

Frequency of the amino-acids, comparing the selected combination A (above) and the natural frequency of all codons.

| Amino-acid | natural frequency | Combination A |
|---|---|---|
| Trp | 1 | 1 |
| Tyr | 2 | 1 |
| Val | 4 | 2 |
| Stop | 3 | 1 |
| Total 21 | 64 | 24 |

Creation of a Set of Four Oligonucleotides According to Combination A

Gene libraries can be created according the requirements of the combination A, by creating four sets of nucleotides in which $X_{n+a}Z_{n+a+1}Z_{n+a+2}$ are:
i) NGG
ii) NCT
iii) NA (A or C)
iv) NT (C or G),
where N is C, G, A or T.

After the synthesis of these oligonucleotides they can be combined to obtain a single-tube cosmix-plexing gene library, whereby to obtain the relative codon frequencies given in Table 2 the gene libraries i) to iv) are present in the final mixture at a ratio of 1:1:2:2, respectively. As explained above this mixture will always give a correct orientation on religation of type IIS restriction enzyme-cleaved fragments having the 2bp single-stranded cohesive ends ZZ.

Alternatively: a Set of Six Oligonucleotides Conforming to Combination A

Gene libraries can be created according a modification of combination A, in which both Stop and cystine codons are eliminated, and in which each of the other amino-acids is each represented by a single codon, by creating six sets of nucleotides in which $X_{n+a}Z_{n+a+1}Z_{n+a+2}$ are:
i) (A, G or T) GG or (C, G or T) GG
ii) NCT
iii) (A, G or C) AA
iv) NAC
v) NTC
vi) ATG After the synthesis of these oligonucleotides they can be combined to obtain a single-tube cosmix-plexing gene library, whereby to obtain the equimolar codon frequencies for each amino-acid the gene libraries i) to vi) are present in the final mixture at a ratio of 3:4:3:4:4:1 respectively. As explained above this mixture will always give a correct orientation on religation of type IIS restriction enzyme-cleaved fragments having the 2bp single-stranded cohesive ends ZZ.

Again, as with the previous sets this single-tube library represents six-subsets which are unable to recombine with each other during cosmix-plexing.

Consideration of the Central Amino-acid Codon Created During Cosmix-plexing Recombination The amino-acid at the recombination site is determined by the 5'-hypervariable segment. The set of amino-acids which may be represented at this position is defined for each subset as presented in Table 2.

Consideration of the Number of Clones Needed in a "Representative" Library

The minimal number of clones required in a library to include all possible amino-acid sequences in a random peptide containing 'n' amino-acids is $20^n$, i.e. for n=9, $20^9=5.12\times10^{11}$. In fact, at a confidence limit of say 95%, this figure must be some three-fold higher, to allow for the statistics of sampling, i.e. ca. $1.5 \times 10^{12}$. In practice this figure may be higher due to, e.g. non-random synthesis of the oligonucleotides used to generate the library as well as biased codon representation (for a detailed discussion see Collins 1997).

Consideration of the Number of Recombined Clones Generated by Cosmix-plexing The cosmix-plexing strategy is based on the concept that in initial selection experiments clone populations will be enriched for sequences which contain structural elements based on the primary sequence in the varied segment. Even if the optimal sequence is not present due to the limitations imposed by the limited size of the initial library, cosmix-plexing will increase the likelihood of finding just such a sequence by providing a large number of novel recombinants in which the 5'- and 3'-"halves" of the varied section are reasserted e.g. for the hypervariable nonapeptide library described in the example, the sequences encoding the amino-proximal five amino acids are recombined with the sequences encoding the carboxy-proximal four amino-acids. Since the cohesive ends essentially limit the recombination to defined subsets, in which one subset cannot undergo recombination with any of the other subsets, the actual number of recombinants generated is less than could be obtained with completely random recombination.

For the initial four-tube protocol described, four separate libraries each containing four subsets are used:

Random recombination would generate, for a set of N clones, $N^2$ recombinants, assuming $N^2$ is less than or equal to the theoretical number of variants ($20^n$, see above) which can be encoded within the hypervariable segment, otherwise it will tend to $20^n$.

For the four-tube protocol 16 subsets are created each representing a pool within which recombination can take place. If the total the library consists of N clones then the number of novel recombinants which can be formed within each of the 16 subsets is $(N/16)^2$. Summing for all sixteen subsets, the number of recombinants which can be generated is $16\times(N/16)^2=N^2/16$, again assuming $N^2/16$ is less than or equal to the theoretical number of variants ($20^n$, see above) which can be encoded within the hypervariable segment, otherwise it will tend to $20^n$.

For the single-tube protocol only 6 subsets are created, each representing a pool within which recombination can take place. If the total library consists of N clones then the number of novel recombinants which can be formed within each of the 6 subsets is $(N/6)^2$. Summing for all six subsets, the number of recombinants which can be generated is $6\times(N/6)^2=N^2/6$, again assuming $N^2/6$ is less than or equal to the theoretical number of variants ($20^n$, see above) which can be encoded within the hypervariable segment, otherwise it will tend to $20^n$.

It is thus clear that the single-tube version of the invention is superior not only in terms of time and economy of the procedure but in the potential to generate a greater diversity from a given number of clones during cosmix-plexing guided recombination.

A specific embodiment of the invention concerns a bank of genes, wherein the six sets of oligonucleotide sequences are present at a ratio of (i):(ii):(iii):(iv):(v):(vi) of (0 to 1):(0 to 1):(0 to 1):(0 to 1):(0 to 1):(0 to 1) with the proviso that at least one of said sets is present.

Further, a specific embodiment of the invention concerns a bank of genes wherein each gene is provided as display vector, especially as M13 phage or M13-like phage or as phagemid.

Further, a specific embodiment of the invention concerns a bank of genes wherein the double stranded DNA sequence is comprised by a DNA region (fusB) encoding a peptide or a protein to be displayed.

Further, a specific embodiment of the invention concerns a bank of genes, characterized in that n=j=6, a=14 and b=16.

Further, a specific embodiment of the invention concerns a bank of genes wherein the restriction enzyme is a type IIS restriction enzyme.

Further, a specific embodiment of the invention concerns a bank of genes which is characterized in that
(a) subsequence $B_1 \ldots B_n$ is the recognition site for the restriction enzyme BpmI (CTGGAG) and subsequence $Q_{n+a+b+1} \ldots Q_{n+a+b+j}$ is an inverted BsgI recognition site (CTGCAC); or
(b) subsequence $B_1 \ldots B_n$ is the recognition site for the restriction enzyme BsgI (GTGCAG) and subsequence $Q_{n+a+b+1} \ldots Q_{n+a+b+j}$ is an inverted BpmI recognition site (CTCCAG).

Further, a specific embodiment of the invention concerns a bank of genes which is characterized in that the hypervariable sequence $X_{n+1} \ldots X_{n+a+b}$ contains NNB or NNK wherein N=adenine (A), cytosine (C), guanine (G) or thymine (T);

B=cytosine (C), guanine (G) or thymine (T); and

K=guanine (G) or thymine (T).

Another embodiment of the invention concerns a phagemid pROCOS4/7 of the sequence shown in FIG. 6.

Still another embodiment of the invention concerns a phagemid pROCOS5/3 of the sequence shown in FIG. 7.

Another embodiment of the invention concerns a method for the production of large
phage-display libraries or
phagemid-display libraries,
containing or consisting of optionally packaged recombined display vectors, wherein recombination takes place at the cleavage site(s) for a restriction enzyme (cut (B) enzyme; arrow in FIG. 3) and wherein
(a) to (b) a double-stranded DNA prepared from Escherichia coli cells containing a display vector population, consisting of M13 phages or M13-like phages or consisting of phagemids according to the invention; a cosmid vector; a restriction enzyme for cut (B); and a restriction enzyme for cut (A) are selected, wherein
(i) the cut (B) enzyme cleaves the display vectors in the region encoding the displayed peptide or displayed protein (arrow in FIG. 3) and generates unique non-symmetrical cohesive ends, wherein each cohesive end is a 2 bp single strand end formed by the two bases designated Z, and
(ii) the cut (A) enzyme cleaves the display vectors and the cosmid vector and generates upon cleavage unique non-symmetrical cohesive ends (fusA) which differ from those resulting from cut (B),
(c) the display vectors are cleaved with the first restriction enzyme,
(d) the display vector and the cosmid vector are cleaved with the second restriction enzyme,
(e) the cleaved display vectors are ligated with the cleaved cosmid vectors forming concatamers,
(f) the ligation product is subjected to a lambda packaging and transduced into an Escherichia coli host,
(g) if wanted, selection is made for a gene present in the ligated display vectors,
(h) the transduced display vectors in the Escherichia coli host are
either in the case of a phage-display vector spontaneously packaged in M13 or M13-like phage coats
or in the case of a phagemid-display vector packaged by infecting the Escherichia coli host with an M13 type helper phage (superinfection),
(i) the packaged display vectors are passaged in a fresh Escherichia coli host and phage-display or phagemid-display libraries are formed and, if wanted,
(j) the passaged display vectors are
either in the case of a phage-display vector spontaneously packaged in M13 or M13-like phage coats
or in the case of a phagemid-display vector packaged by infecting the fresh Escherichia coli host with an M13 type helper phage (superinfection) and
phage-display or phagemid-display libraries are formed.

A specific embodiment of the invention concerns a method which is characterized in that in steps (a) to (b) a type IIS restriction enzyme is selected, preferably BgII, DraIII, BsgI or BpmI.

Further, a specific embodiment of the invention concerns a method which is characterized in that for cuts (B) and (A) the same restriction and/or restriction enzyme is selected.

Further, a specific embodiment of the invention concerns a method which is characterized in that as cut (B) enzyme and as cut (A) enzyme different enzymes are used (FIG. 3), preferably BsgI or BpmI as cut (B) enzyme and DraIII as cut (A) enzyme (fd or M13 replication origin cut).

Further, a specific embodiment of the invention concerns a method which is characterized in that in step (h) and facultatively in step (j) M13K07 is used as M13 type helper phage.

Further, a specific embodiment of the invention concerns a method which is characterized in that the phagemid and the cosmid are identical and, further, presence of and cleavage with cut (A) enzyme is optional and/or cut (B) enzyme and cut (A) enzyme are identical.

Further, a specific embodiment of the invention concerns a method which is characterized in that in step (i) the multiplicity of infection (MOI) is less than or equal to 1.

Further, a specific embodiment of the invention concerns a method wherein the cosmid comprises an fd or M13 bacteriophage origin (replication/packaging).

Further, a specific embodiment of the invention concerns a method wherein in step (e) a mol ratio of display vectors to the cosmid vector within the range of from 3:1 to 15:1 and preferably 3:1 to 10:1 is used.

Further, a specific embodiment of the invention concerns a method wherein in step (e) a vector concentration (comprising display vectors and cosmid vectors) of more than 100 µg DNA/ml is used.

Another embodiment of the invention concerns a method for the production of large
phage-display extension libraries or
phagemid-display extension libraries, wherein an oligonucleotide cassette of d bases in length is inserted into a restriction site (cut (B)) via the cohesive ends ZZ as defined above to yield a sequence (supra sequence) or a gene comprising a double stranded DNA sequence which is represented by the following formula of one of their strands:

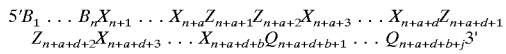

$5'B_1 \ldots B_n X_{n+1} \ldots X_{n+a} Z_{n+a+1} Z_{n+a+2} X_{n+a+3} \ldots X_{n+a+d} Z_{n+a+d+1}$
$Z_{n+a+d+2} X_{n+a+d+3} \ldots X_{n+a+d+b} Q_{n+a+d+b+1} \ldots Q_{n+a+d+b+j} 3'$ wherein d is an integer and a multiple of 3, preferably within the range of from 6 to 36; n, a, b and j and B, X, Z and Q have the same meaning as in any of the preceding claims; and wherein (a) to (b) a double-stranded DNA prepared from *Escherichia coli* cells containing a display vector population, consisting of M13 phages or M13-like phages or consisting of phagemids according to the invention; a cosmid vector; a restriction enzyme for cut (B); and a restriction enzyme for cut (A) are selected, wherein (i) the cut (B) enzyme cleaves the display vectors in the region encoding the displayed peptide or displayed protein and generates unique non-symmetrical cohesive ends; wherein each cohesive end is a 2 bp single strand end formed by the two bases designated Z, (ii) the cut (A) enzyme cleaves the display vectors and the cosmid vector such that unique non-symmetrical cohesive ends are formed which differ from those resulting from cut (B), (c1) the display vectors are cut with the cut (B) restriction enzyme, (c2) a DNA cassette is inserted into the cleavage site with their ZZ cohesive ends, (d) the resulting display vector and the cosmid vector are cleaved with the cut (A) restriction enzyme, (e) the cleaved display vectors are ligated with the cleaved cosmid vectors forming concatamers, (f) the ligation product is subjected to a lambda packaging and transduced into an *Escherichia coli* host such that the DNA cassette lies between two hypervariable sequences (extension sequences), (g) if wanted, selection is made for a gene present in the ligated display vectors, (h) the transduced display vectors in the *Escherichia coli* host are either in the case of a phage-display vector spontaneously packaged in M13 or M13-like phage coats or in the case of a phagemid-display vector packaged by infecting the scherichia coli host with an M13 type helper phage (superinfection), (i) the packaged display vectors are passaged in a fresh *Escherichia coli* host and phage-display or phagemid-display libraries are formed, and, if wanted, (j) the passaged display vectors are either in the case of a phage-display vector spontaneously packaged in M13 or M13-like phage coats or in the case of a phagemid-display vector packaged by infecting the fresh *Escherichia coli* host with M13 type helper phages (superinfection) and phage-display or phagemid-display extension libraries are formed.

Another embodiment of the invention concerns a method for the reassortment of the 5'- and/or 3'-extensions in the production of large recombinant phage-display extension libraries or phagemid-display extension libraries, comprising the sequence as defined before wherein recombination takes place at one or the other, or consecutively at both the cleavage site(s) ZZ bracketing the inserted cassette(s), wherein (a) to (b) a double-stranded DNA prepared from *Escherichia coli* cells containing a display vector population, consisting of M13 phages or M13-like phages or consisting of phagemids as display vectors as defined before; a cosmid vector; a restriction enzyme for cut (B); and restriction enzyme for cut (A) are selected, wherein (i) the cut (B) enzyme cleaves the display vectors in the region encoding the displayed peptide or displayed protein and generates unique non-symmetrical cohesive ends at selectively either the 5'-junction of extension and cassette (cleavage by the restriction enzyme recognizing the binding site $B_1 \ldots B_n$ as defined before), or at the 3'-junction of extension and cassette (cleavage by the restriction enzyme recognizing the binding site $Q_{n+a+b+1} \ldots Q_{n+a+b+j}$ as defined before, or $Q_{n+a+d+b+1} \ldots Q_{n+a+d+b+j}$ as defined before), wherein each cohesive end is a 2 bp single strand end formed by the two bases designated Z, (ii) the cut (A) enzyme cleaves the display vectors and the cosmid vector and generates upon cleavage unique non-symmetrical cohesive ends which differ from those resulting from cut (B), (b) the display vectors are cleaved with the first restriction enzyme, (c) the display vector and the cosmid vector are cleaved with the second restriction enzyme, (e) the cleaved display vectors are ligated with the cleaved cosmid vectors forming concatemers, (f) the ligation product is subjected to a lambda packaging and transduced into an *Escherichia coli* host, (g) if wanted, selection is made for a gene present in the ligated display vectors, (h) the transduced display vectors in the *Escherichia host* are either in the case of a phage-display vector spontaneously packaged in M13 or M13-like phage coats or in the case of phagemid-display vectors packaged by infecting the *Escherichia coli* host with an M13-type helper bacteriophage (superinfection), (i) the packaged display vectors are passaged in a fresh *Escherichia coli* host and phage-display or phagemid-display libraries are formed and, if wanted (j) the passaged display vectors are either in the case of a phage-display vector spontaneously packaged in an M13 or M13-like phage coats or in the case of a phagemid vector packaged by infecting the fresh *Escherichia coli* host with M13 type helper phages (superinfection) and phage-display or phagemid-display libraries are formed.

A specific embodiment of the invention concerns a method which is characterized in that in steps (a) to (b) a type IIS restriction enzyme is selected, preferably BglI, DraIII, BsgI or BpmI.

Further, a specific embodiment of the invention concerns a method which is characterized in that for cuts (i) and (ii) the same restriction site is selected.

Further, a specific embodiment of the invention concerns a method which is characterized in that as cut (B) enzyme and as cut (A) enzyme different enzymes are used, preferably BsgI or BpmI as cut (B) enzyme and DraIII as cut (A) enzyme (fd or M13 replication origin is cut).

Further, a specific embodiment of the invention concerns a method which is characterized in that in step (h) and facultatively in step (j) M13K07 is used as the M13-type helper phage.

Further, a specific embodiment of the invention concerns a method which is characterized in that in step (g) selection is made for the presence of an antibiotic resistance gene.

Further, a specific embodiment of the invention concerns a method which is characterized in that in step (i) the multiplicity of infection (MOI) is less than or equal to 1.

Further, a specific embodiment of the invention concerns a method wherein the cosmid comprises an fd or M13 bacteriophage origin.

Further, a specific embodiment of the invention concerns a method wherein in step (e) a mol ratio of display vectors to the cosmid vector within the range 3:1 to 15:1 and preferably 3:1 to 10:1 is used.

Further, a specific embodiment of the invention concerns a method wherein in step (e) a vector concentration (comprising display vectors and cosmid vectors) of more than 100 μg DNA/ml is used.

Another embodiment of the invention concerns a method for the de novo production of large phage-display libraries or phagemid-display libraries, comprising DNA sequences as defined before, and subjectable to recombination according to a procedure as defined before, wherein recombination takes place within a DNA sequence as defined before, wherein a) a display vector, consisting of an M13 phage or M13-like phage or consisting of a phagemid-display vector comprising a bacteriophage replication origin, facultatively a gene for a selectable marker, preferably an antibiotic resistance, a lambda bacteriophage cos-site and a "stuffer"-sequence (FIG. 5 upper right), containing two binding sites for a type IIS restriction enzyme different from any of the enzymes as defined before (cut (B) and cut (A)), wherein said two sites are oriented in divergent orientation and where the cohesive ends generated on cleavage are non-symmetrical and differ from one another at the two sites, and b) a PCR-generated fragment comprising part of one of the sequences as defined before, including a (the) hypervariable sequence(s), preferably $X_{n+1} \ldots X_{n+a}Z_{n+a+1}Z_{n+a+2}X_{n+a+3} \ldots X_{n+a+b}$ according to the invention, bracketted by the same type IIS restriction enzyme binding sites defined in (a), but in this case both oriented inwards towards the hypervariable sequence (FIG. 5 left side) and where on cleavage by this restriction enzyme two non-symmetrical, single strand ends different from one another are generated, where the first end (a' in FIG. 5) is complementary to one of the ends (a in FIG. 5) generated on the large vector fragment in (a) and the second end (b' in FIG. 5) is complementary to the other end (b in FIG. 5) generated on the large vector fragment in (a), c) the two cleavage reaction systems (a) and (b) still containing the active type IIS restriction enzyme are mixed together in approximately equimolar proportions and subjected to ligation in the presence of DNA ligase;

fragments containing the restriction enzyme binding sites are constantly removed ("stuffer" fragment and outer end of the PCR product) whereas the other two components, namely the large vector fragment and the insert sequence (central fragment from the PCR reaction) are driven to form A) a concatameric hybrid if the ligation is carried out at >100 μg DNA/ml (FIG. 5), or B) a circular hybrid if the ligation is carried out at < or=40 μg DNA/ml, d1) in the case of protocol A) the DNA is packaged into lambda particles and transduced into an *Escherichia coli* host, d2) in the case of protocol B) the DNA is transformed in an *Escherichia coli* host, e) if wanted, selection is made for a gene present in the ligated display vectors, f) the transduced display vectors in the *Escherichia coli* host are either in the case of a phage-display vector spontaneously packaged in M13 or M13-like phage coats or in the case of phagemid-display vectors packaged by infecting the *Escherichia coli* host with an M13-type helper bacteriophage (superinfection), (g) the packaged display vectors are passaged in a fresh *Escherichia coli* host and phage-display or phagemid-display libraries are formed and, if wanted (h) the passaged display vectors are either in the case of a phage-display vector spontaneously packaged in an M13 or M13-like phage coats or in the case of a phagemid vector packaged by infecting the fresh *Escherichia coli* host with M13-type helper phages (superinfection) and phage-display or phagemid-display libraries are formed.

A specific embodiment of the invention concerns a method which is characterized in that in steps (a) to (b), as type IIS restriction enzyme, preferably BpiI, BsgI or BpmI is selected.

Further, a specific embodiment of the invention concerns a method which is characterized in that in step (f) and facultatively in step (h) M13K07 is used as the M13-type helper phage.

Further, a specific embodiment of the invention concerns a method which is characterized in that in step (e) selection is made for the presence of an antibiotic resistance gene.

Further, a specific embodiment of the invention concerns a method which is characterized in that in step (g) the multiplicity of infection (MOI) is less than or equal to 1.

Another embodiment of the invention concerns a phage-display library or a phagemid-display library in the form of packaged particles obtainable according to any of the methods as described before.

Another embodiment of the invention concerns a phage-display library or a phagemid-display library in the form of display vectors comprised by *Escherichia coli* population(s) obtainable according to any of the methods as described before.

Another embodiment of the invention concerns a phage-display libraries or phagemid libraries which are characterized by a gene (genes) as defined before and obtainable according to the invention, wherein the term "large" as used before is defined as in excess of $10^6$ variant clones, preferentially $10^8$ to $10^{11}$ variant clones.

Finally, another embodiment of the invention concerns a protein or peptide comprising a peptide sequence encoded by a DNA sequence as defined before and obtainable by affinity selection procedures on a defined target by means of libraries as defined before.

DETAILED DESCRIPTION

The invention pertains to a novel combination of recombinant DNA technologies to produce large hypervariable gene banks for the selection of novel ligands of pharmaceutical, diagnostic, biotechnological, veterinary, agricultural and biomedical importance with an efficiency higher than was hitherto attainable.

The size of the hypervariable gene bank is presently considered the most essential factor limiting the usefulness of the methodology for such purposes, since, as an empirical method, it depends on the diversity (number of different variants) initially generated in the bank (hypervariable gene library). In contrast to this traditional opinion we consider that, when a highly efficient method is developed, as presented here, to generate a large proportion of the possible combinations of mutated segments of the variants from a preselected subpopulation, a population enriched for the desired structural elements will be generated which would only have been represented in a population approaching $N^x$ where N is the size of the original population and x is the number of segments to be recombined.

The first part of the invention pertains to novel sequences which allow recombination within hypervariable DNA sequences encoding regions (domains) variable peptides or proteins displayed in combinatorial phage/phagemid display libraries using type IIS restriction endonucleases both (a) to introduce a cut at the site of recombination and (b) to generate oriented substrates for a ligation reaction, where the ligation products are then recloned at high efficiency after in vitro packaging in a lambda packaging mix. The entire protocol yields efficiencies (clones per input DNA) in excess of any described technology ($>10^8$ clones per microgram ligated DNA).

Combinations of (vector) sequences and protocols are claimed for both the production of the initial libraries and for recombinational procedures to generate increased diversity within the library or a selected subpopulation at any time. In particular such sequences and procedures are claimed for the generation and use of phage/phagemid-display combinatorial libraries.

The inventors recognize that the main factor thereby determining the efficient generation of further variation is the efficient production of combinatorial libraries from the initial libraries, via reassortment of smaller elements (specific peptide sequences within the hypervariable region, and/or reassortment of structural domains) which contribute to the properties selected for. The invention presents such a method, which has the unique property that the recombination site may be within the hypervariable region whereby no restriction is imposed on the sequence within the hypervariable region involved. Alternatively the method can be used to reassort domains of proteins or subunits of heteromeric proteins (proteins composed of two or more different variant polypeptide chains), each of which can contain hypervariable regions, without resorting to recloning isolated DNA fragments or generating new libraries containing new synthetic oligonucleotides. It is noted that this method thus offers a saving in both time and materials when optimizing a structure for a predetermined property on the basis of a preselected clone population (subpopulation) and in view of the geometrical increase in possible variability offered may represent a qualitatively novel feature in that some rare structures may be obtainable only by the novel strategy described.

The method, we designate cosmix-plexing[7], is based on the design of the cloning vectors, the inserts used and a combination of special recombinant DNA protocols, which in particular use i) cleavage of the phage/phagemid DNA with type IIS restriction enzymes, ii) subsequent ligation to concatamers which are iii) packaged in vitro with a lambda packaging system for iv) efficient transduction into E. coli strains, where they are then v) repackaged in vivo in filamentous phage coats. The use of cosmix-plexing[7], so defined, on a heterogeneous phage/phagemid population generates an enormous increase in novel variants at any time during further experimentation, e.g. after any enrichment step for structures having the predetermined property or properties.

In particular subpopulations which are enriched from the original library for a specific property will be enriched for a consensus motif (a degenerate set of related sequences within the varied region(s) which all exhibit the required property to some extent) which may (probably will) include the optimal sequence in terms of the required property. Reassortment of these regions or portions of a single hypervariable sequence by cosmix-plexing[7] will increase the probability of obtaining the optimal sequence. The subpopulations may be isolated by differential affinity-based selection on a defined target, or enrichment procedures based on other desired selectable properties (example 1: substrate properties such as phosphorylation by a particular protein kinase enriched by binding on antibodies which recognize the modified (in this case phosphorylated)substrate; or example 2: cleavage of the variant sequence by an endoprotease, using selective release of the phage or phagemid previously bound via an interaction between a terminal protein structure (anchor) and its ligand immobilized to, or later trapped on, a surface).

The invention further covers the generation of extension libraries in which e.g. a "project-specific cassette" is inserted at the recombination site within the gene bank. Optimisation of ligands can then occur by the generation of further combinatorial libraries from selected clones in which the adjacent regions may be efficiently "shuffled", either singly or both at a time. As far as we are aware no other system provides this "cassette" insertion/exchange" feature.

Double-stranded phagemid from a number of clones (which may be a cosmid itself) and cosmid DNA (if the phagemid is not a cosmid) are cleaved with a type IIS restriction enzyme (cleavage sites indicated by a small bar) within the hypervariable region and ligated together at high DNA concentration so that long concatemers of the DNA molecules are formed, which are all oriented in the same direction, e.g. with respect to the M13 packaging origins, i.e. no palindromic regions are formed. The vectors contain one or more restriction site(s) for the type IIS restriction enzyme such that no cohesive ends are formed which on ligation could form palindromic (i.e. head-to-head or tail-to-tail) structures. When the cohesive ends produced on cleavage by the restriction enzyme are themselves non-palindromic and unique to each restriction site within each plasmid/phagemid, only ring closure and the formation of concatemers can be formed. At higher DNA concentrations (i.e. over 200 µg/ml) concatemer formation will be preferred. A more detailed presentation of the molecular structures formed is given in FIGS. 2 and 3. The ligation product is added to an in vitro lambda packaging extract where the DNA is packaged into a lambda bacteriophage coat as a linear DNA of 37 to 50 kb cleaved at a lambda cos-site. In the following step, referred to as transduction, these particles carrying the cosmid-phagemid hybrid DNA are added to *Escherichia coli* cells (shown as large ellipses in the diagram) into which the DNA injects itself. In the cell it is circularized by closure of the cleaved cos-site using the endogenous DNA ligase. It is then propagated as a large cosmid-phagemid hybrid, replicating from the plasmid DNA replication origin(s). M13-type helper phage (e.g. M13K07) is added to these cells in the step referred to as superinfection. On entry of the helper phage single strand replication is initiated from the M13 replication origins present in the individual copies of the phagemid contained in the concatemer. During this process the phage are also packaged into M13 coats, and secreted into the medium. The phagemid can be harvested from the supernatant of the culture. A second passage, i.e. transduction into an *E. coli* host and repackaging by superinfection with helper phage is necessary before these phagemid are used in a selection procedure in order to ensure that a particular variant protein is presented only on the particle carrying the gene for that particular variant protein. It is noted that this is a highly efficient process in which a yield of more than 108 different phagemid can be produced pro microgram of ligated input DNA.

Figure 1:
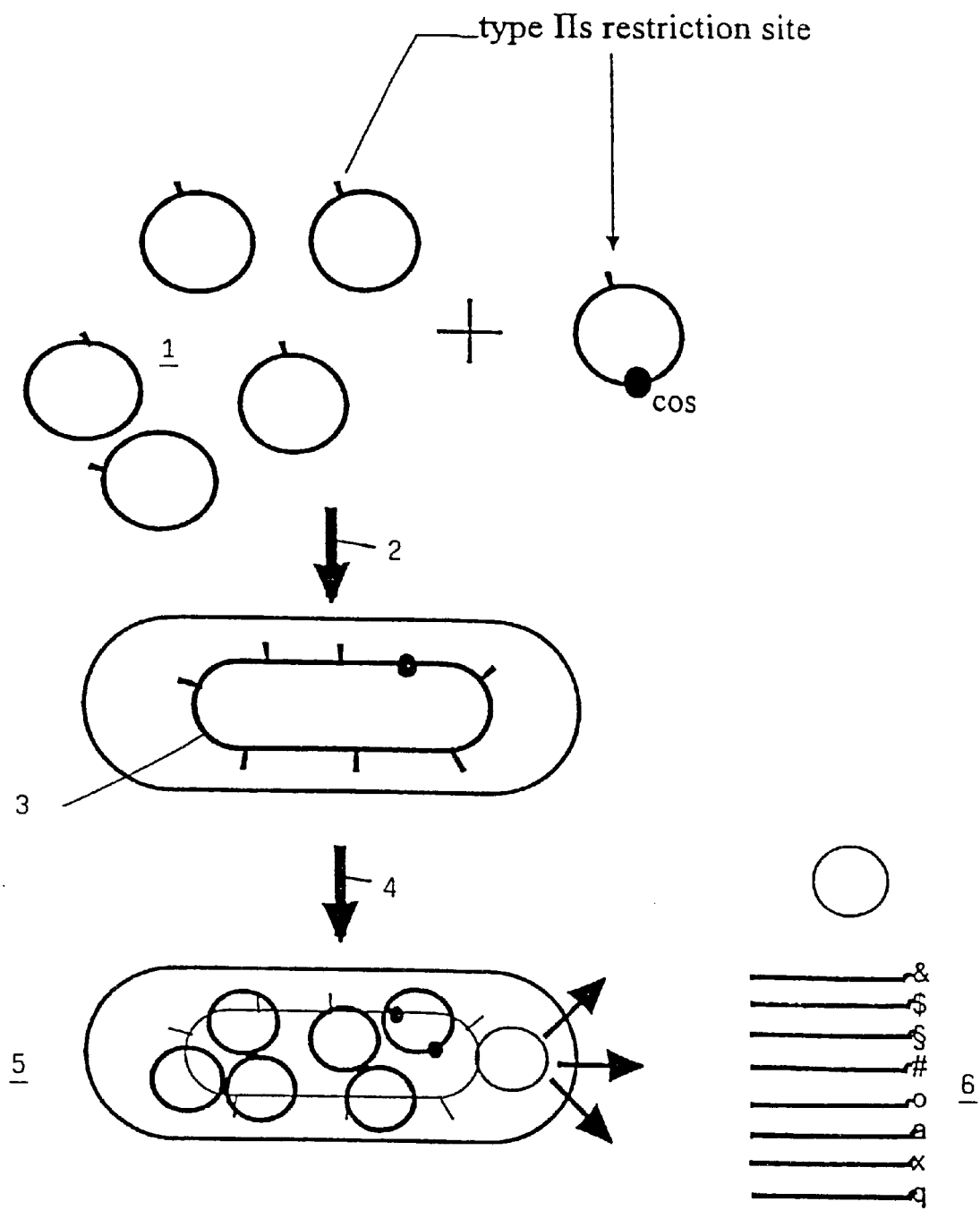
FIG. 1. Diagrammatic representation of the steps involved in creating recombination within the hypervariable regions of cosmix-plexing[7] libraries.
Figure 2:
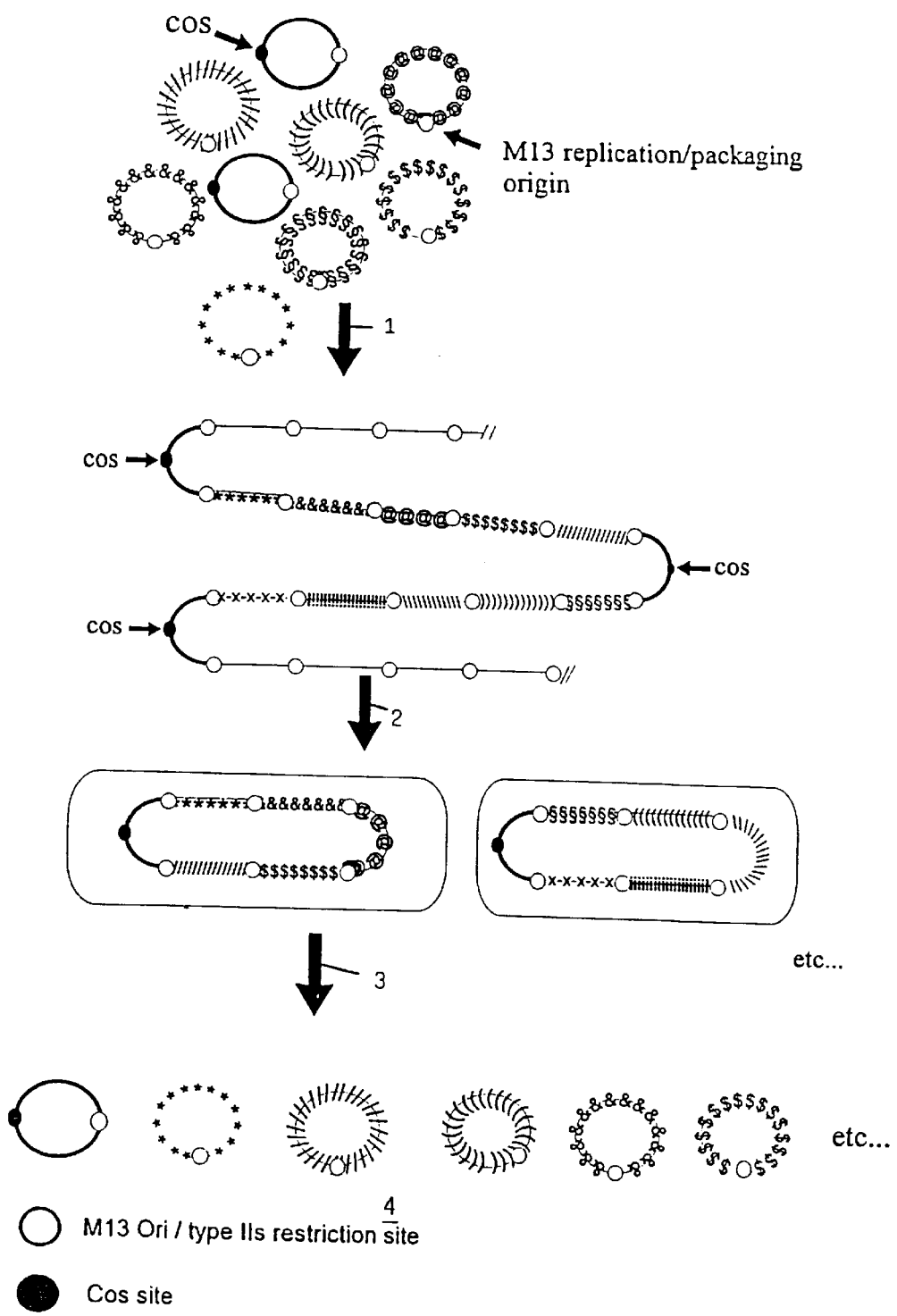

FIG. 2. The diagram illustrates the DNA structures formed when the cosmix-plexing[7] protocol is carried out as shown in FIG. 1. Different variants are designated by different patterns for the whole plasmid. Initially double-stranded DNA is cleaved with a type IIS restriction enzyme A. The ligation product is illustrated as a concatemer in which each phagemid is oriented in the same orientation. The products of 37 to 50 kb introduced after in vitro lambda packing and introduction into the *E. coli* cells (shaded ellipses) are shown, whereby, for example 8 to 10 copies of a 4.5 kb phagemid may be present per cell. On repackaging the same phagemid are obtained as were present before cleavage and ligation. The protocol as shown here in which the M13-packaging/replication site and the restriction site for enzyme A are identical, is simply an efficient method of amplification when starting with double stranded DNA.

Figure 3:
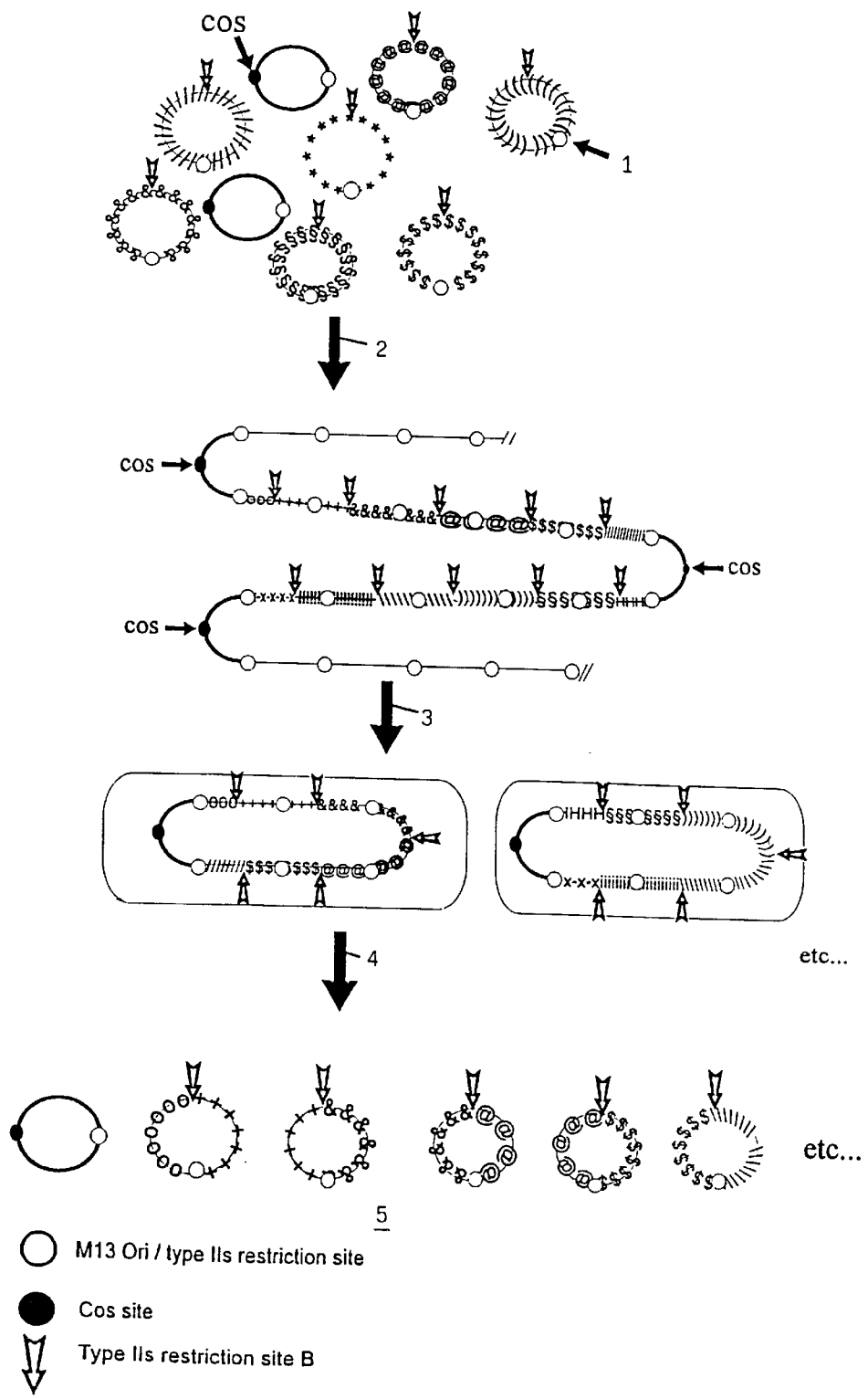

FIG. 3. The diagram illustrates a variant of the protocol illustrated in FIGS. 1 and 2 in which recombination is achieved between different phagemid variants. The crossover point for the recombination is the cleavage site for the type IIS restriction enzyme B (shown as a hollow arrow) cleaving preferentially within a hypervariable region or between two different variable regions (see also FIG. 4, where additional cleavage sites within other variable regions may be recombined simultaneously). Again, as mentioned in the FIG. 1 legend, each phagemid may be a cosmid itself, in which case the addition of another cosmid is unnecessary. In this example cleavage with the restriction enzyme A is optional. Although FIGS. 2 and 3 are almost identical it should be noted that the products of the scheme in FIG. 3 are all recombined, i.e. hybrids of the two sides of different variants. Repassaging is needed before use in the recombined library for selection experiments for the same reasons discussed in the previous two Figures.

Figure 4:
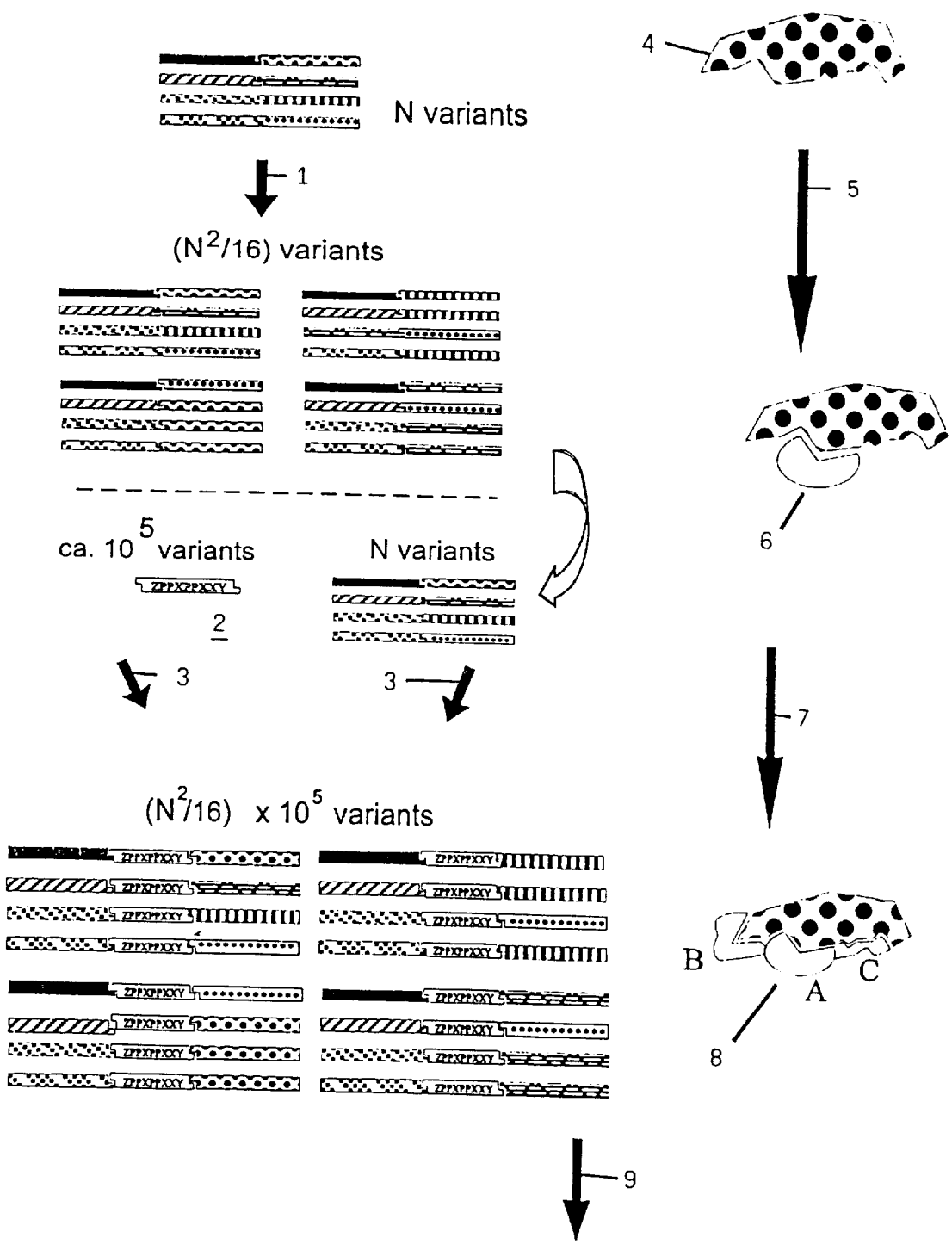

FIG. 4. Cosmix-plexing[7] strategies.

The left part of the figure shows the hypervariable DNA sequences encoding the variable portion of the peptide or protein presented on the phage/phagemid. The four bars designated 'N variants' show that there are different sequences on either side of the type IIS restriction cleavage site. Phagemid DNA from the variant clones can be cleaved with the type IIS restriction enzyme and religated to yield the indicated number of recombinant clones, within the limits of the cloning efficiency. If one starts with a subpopulation of preenriched variants from the primary library (say $4 \times 10^4$ clones) then one-sixteenth of all possible recombinants ($10^8$) can be obtained.

The construction of "extension libraries" is shown below the dotted line. In this case a project-specific cassette containing a biased codon distribution encoding some sequence elements previously defined as advantageous for binding to the target is inserted into the hypervariable sequence at the type IIS restriction cleavage site. The large library thus generated encodes a protein containing three segments (domains B, A and C), whereby the central domain A is encoded by the project-specific cassette, and is bordered by the hypervariable domains B and C.

The formuli for the numbers of variants obtained are made for the protocol in which four separate libraries are constructed.

The right side of the figure illustrates how the variant protein might bind to a target protein. The variants selected from the extension library are expected to have a larger surface of interaction and thus to exhibit stronger and/or more specific binding to the defined target. The target may be a cell, a (partially) purified protein or peptide e.g. enzyme, antibody, hormone or lymphokine, cell receptor or in fact any defined surface or particle suspension, possibly coated with one of the aforementioned targets, which is amenable to physical separation, i.e. the wall of a receptacle (tube, tubing, flask, microtiter plate, a planar surface), or a particle (e.g. beads, magnetic beads, or droplets in a two-phase liquid system).

Figure 5:
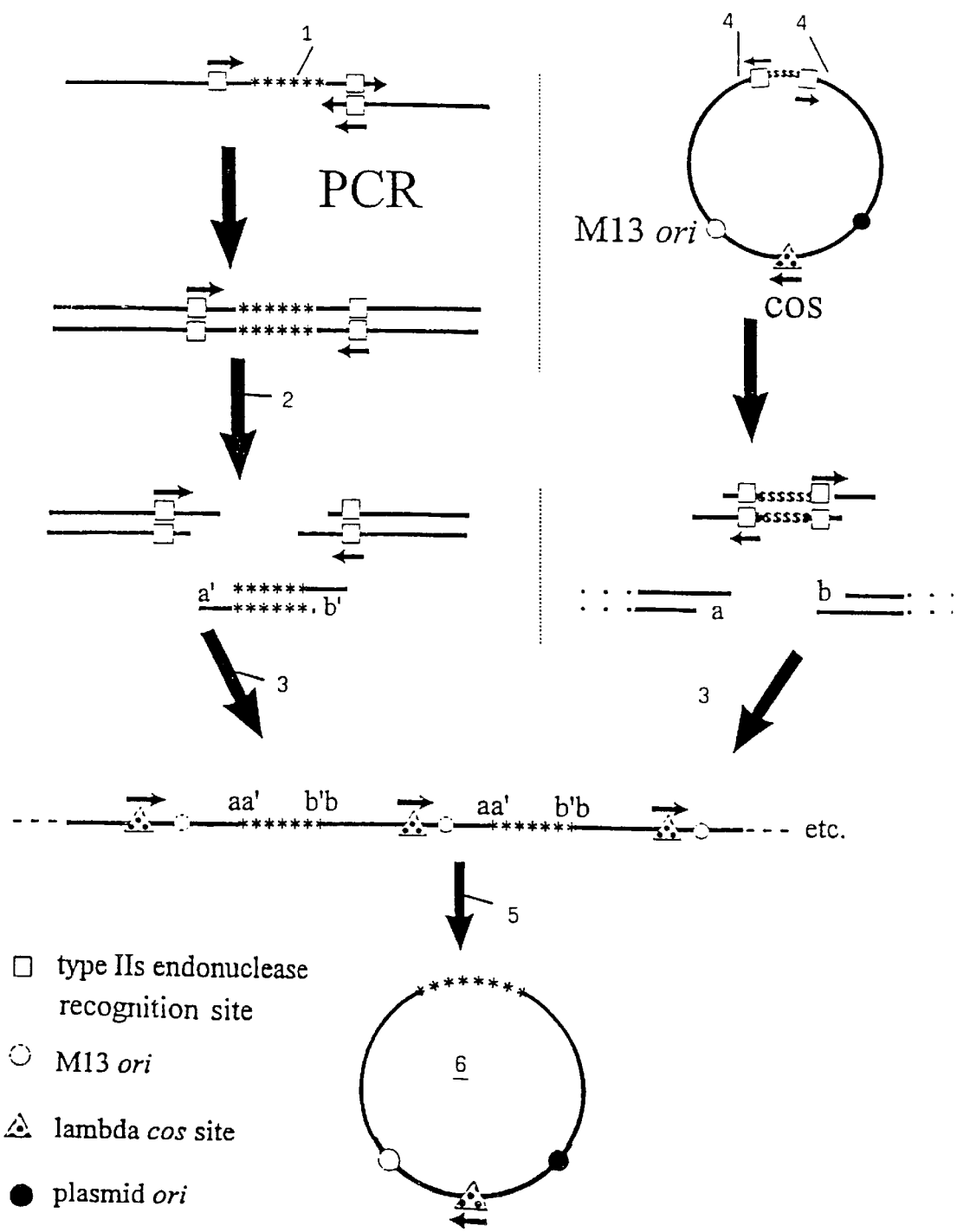

FIG. 5: Driven directed cloning (DDC)

This figure illustrates an example of a cloning protocol which has excellent properties for the highly efficient construction of hypervariable libraries and extension libraries, which can be used with the cosmix-plexing7 method. The left side of the figure shows the preparation of the hypervariable cassette to be inserted into the cosmid-phagemid double-stranded vector. The cosmid-phagemid vector containing a "stuffer fragment" is shown on the right. Both the PCR-product containing the hypervariable sequence, shown as a line of asterisks, and the vector containing the "stuffer" are cleaved with the same type IIS restriction enzyme(s). It is noted that the recognition sites for this (these) enzyme(s) are oriented in opposite directions, i.e. outwards from the stuffer in the case of the vector, and inwards in the case of the PCR-product. After cleavage neither the hypervariable cassette to be inserted nor the vector contain any of the original type IIS restriction enzyme recognition sites. The vectors and insert are, however, designed to have non-palindromic cohesive ends at their termini, generated by the restriction enzyme cleavage, so that a ligation of insert and vector leads to an oriented insertion of the hypervariable region. In addition, the vector cannot undergo ring closure in the absence of the insert cassette nor can the insert fragments ligate to one another. Since the ligation is carried out at high DNA concentration and in the continued presence of the restriction enzyme any ligation product resembling in the initial uncleaved or partially cleaved vector or PCR-product will be immediately recleaved. This combination of oriented non-palindromic cohesive ends and recleavage of unwanted ligation products, drives, especially at high DNA concentration, where the formation of ring closure of a vector-insert-hybrid is at a disadvantage, the formation of oriented double-stranded concatemers of the structure required for highly efficient cosmid packaging. The primary cosmix-plexing library is formed finally by transducing the packaged cosmid-phagemid hybrids into an *E. coli* host which contains, or is superinfected with, an M13-like helper phage. The phagemid are repassaged in a second M13 phage-packaging step before use in selection so that individual phage clones are derived from singly infected cells. This is necessary in order that each phagemid particle carries the variant encoded in its genome.

This is not the situation in the first packaging step in which the *E. coli* host contains a concatemer of some eight different variant phagemid.

The use of hypervariable sequences in the description of the invention implies in general that we try to use set of oligonucleotides in which "randomized sequences" encode amino acids at ratios near to that normally found in natural proteins, whereby the frequency of stop-codons is reduced. We are aware that for certain applications biased subsets may be preferable in the construction of dedicated sublibraries.

Figure 6A:
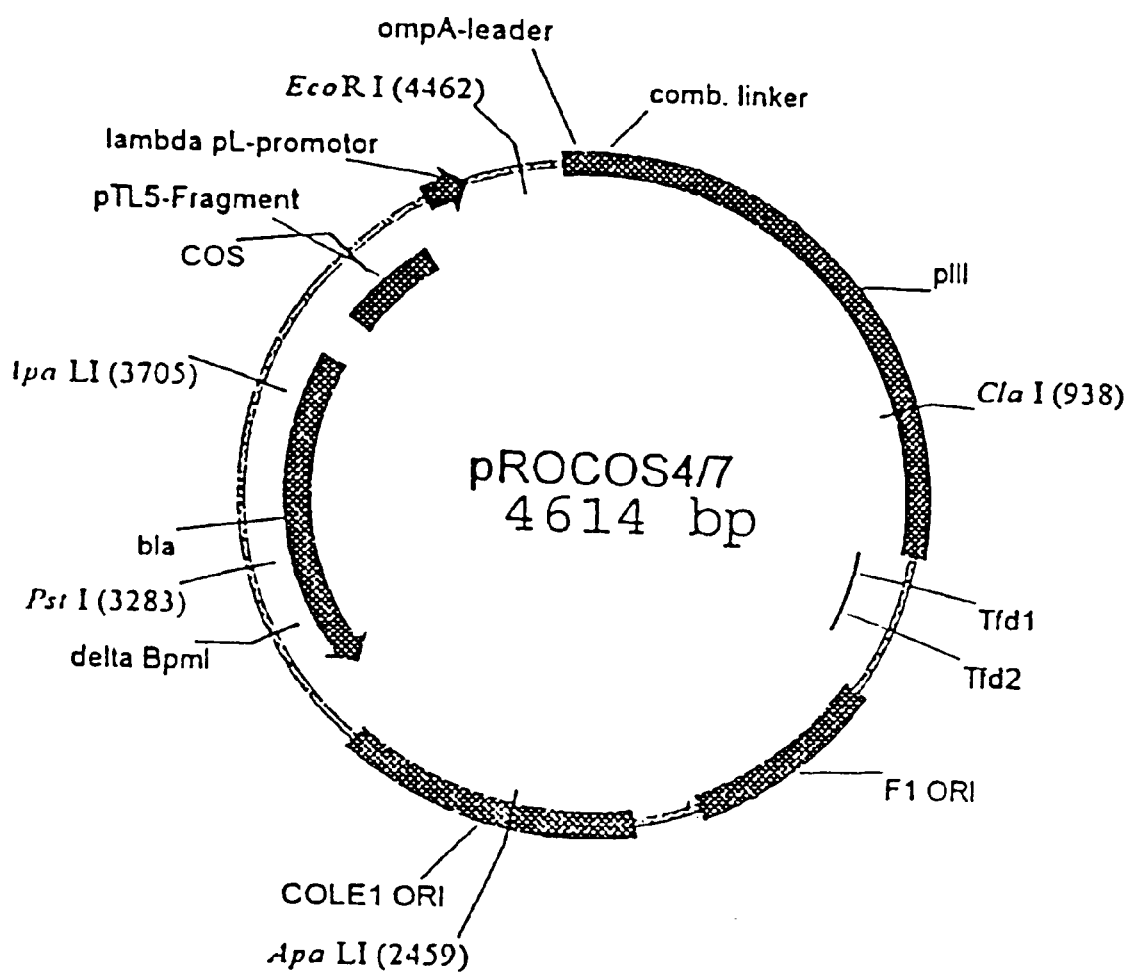

FIG. 6 The diagram in FIG. 6A shows a diagram of the phagemid pROCOS4/7. FIG. 6B through FIG. 6E shows the sequence of the phagemid pROCOS4/7 (SEQ ID NO:17).

Figure 7A:
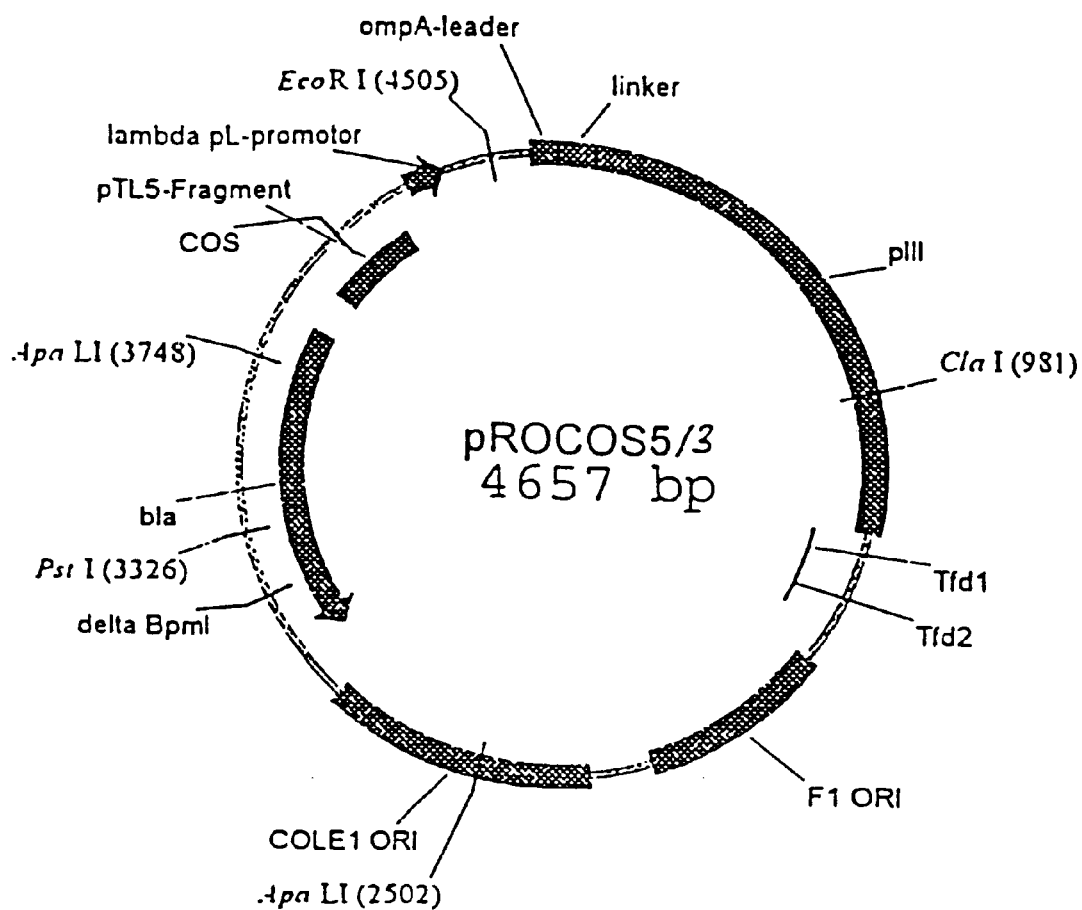

FIG. 7 The diagram in FIG. 7A shows a diagram of the phagemid pROCOS5/3. FIG. 7B through FIG. 7E shows the sequence of the phagemid pROCOS5/3 (SEQ ID NO:18).

EXAMPLE 1

Cosmix-plexing Using the Four-tube Method
(According to Claims 1–10)

1a) Library Generation

Oligonucleotide Sequences:

```
NONA-CA:

5' TCGGGGTACCTGGAGCA(XNN)4 KKN(XNN) GCTGCACGGGAGCTCGCC 3'
        KpnI                                  SacI

NONA-CT:

5' TCGGGGTACCTGGAGCA(XNN)4 RRN(XNN) GCTGCACGGGAGCTCGCC 3'

NONA-GA:

5' TCGGGGTACCTGGAGCA(XNN)4 YYN(XNN) GCTGCACGGGAGCTCGCC 3'

NONA-GT:

5' TCGGGGTACCTGGAGCA(XNN)4 MMN(XNN)4 GCTGCACGGGAGCTCGCC 3'
```

Recombination can be achieved within the hypervariable region of the gene encoding the protein or peptide presented on the phagemid according to the scheme illustrated in FIG. 1. With extension libraries, either the left (5') or right (3') extension, or both, can be reassorted by cleaving with a type IIS restriction enzyme recognizing a site bordering either left end, the right end (opposite orientation), or both ends respectively, as described for the sequences $B_1$-$B_n$ and $Q_{n+a+1} \ldots Q_{n+a+1}$ in claim 3.

where X means: A, C and G; N: A, C, G and T; K: G and T; R:G and A; Y: C and T; M: C and A.
NONA PCR-L (SEQ ID NO:5):
5' GGCGAGCTCCCGTGCAGC 3'
NONA PCR-R (SEQ ID NO:6):
5' TCGGGGTACCTGGAGCA 3'
KpnI (GGTACC) and SacI (GAGCTC) restriction enzyme recognition sites are marked in bold type.

important vector DNA-Sequences:

```
pROCOS4/7:
                                    Eco47 111
         SacI    BsgI      KpnI              |pIII→
5' GGCGAGCTCCCGTGCAGCGCTCCAGGTACCCCGATATCAGAGCTGAA 3'
                          BpmI
``` pROCOS4/7-Stuffer1 (SEQ ID NOS:8,9)

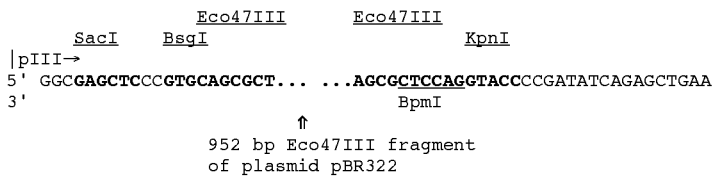

KpnI (GGTACC), SacI (GAGCTC), BsgI (GTGCAG), Eco47III (AGCGCT) and BpmI (CTGGAG) restriction enzyme recognition sites are marked in bold type. The first codon of the mature pIII protein (GAA) is indicated.

For the generation of double-stranded DNA inserts the single-stranded hypervariable DNA oligos NONA-CA, NONA-CT, NONA-GA and NONA-GT are amplified using the single stranded DNA oligos NONA PCR-L and NONA PCR-R as PCR-primers according to the following protocol:

Remark: the four hypervariable DNA-oligos have to be kept strictly separated!

PCR-Amplification of DNA Oligos
PCR-buffer (10×):

| KCl | 500 mM |
| Tris-HCl (pH 9.0) | 100 mM |
| Triton X-100 | 1% |

Taq DNA polymerase (Promega) in storage buffer A:

| glycerol | 50% |
| Tris-HCl (pH 8.0) | 50 mM |
| NaCl | 100 mM |
| EDTA | 0.1 mM |
| DTT | 1 mM |
| Triton X-100 | 1% |
| TE-buffer (1X) | |
| Tris-HCl (pH 8.0) | 10 mM |
| EDTA | 0.1 mM |

1. Transfer 2 µl of a 10 pmol/µl solution of the hypervariable oligos NONA-CA, -CT, -GA and -GT in a 0.2 ml PCR reaction tube (4 tubes).
2. Mix the following in one Eppendorf reaction tube:

| ddH$_2$O | 276.75 µl |
| PCR-buffer (10X) | 45.0 µl |
| NONA PCR-L (100 pmol/µl) | 9.0 µl |
| NONA PCR-R (100 pmol/µl) | 9.0 µl |
| dNTPs (10 mM each) | 9.0 µl |
| Taq DNA polymerase (5 U/µl) | 2.25 µl |

3. Transfer 78 µl of this mixture to each of the PCR tubes containing the hypervariable oligos (step 1).
4. Mix 45 µl MgCl$_2$ (25 mM) and 45 µl ddH$_2$O in an Eppendorf reaction tube.
5. Preheat a PCR thermocycler to 94° C. (if possible use a heated lid).
6. Transfer 20 µl of the MgCl$_2$ solution (step 4) into each of the PCR tubes (step 3).
7. Put the tubes directly into the thermocycler (simplified hot-start) and run the following program:
   1. 94° C. 30sec
   2. 94° C. 10 sec
   3. 52° C. 10 sec
   4. repeat 9 times step 2 and 3
   5. hold at 4° C.
8. Take an aliquot of 5 µl to run a 4.5% agarose gel.
9. Add 200 µl ddH$_2$O to each tube, extract with phenol, precipitate with ethanol and resuspend the DNA in 120 µl TE-buffer.

For cloning the amplified oligo-DNA are cut with KpnI and SacI. Also the vector-DNA has to be cut with both enzymes. As vector-DNA pROCOS4/7 or a derivative thereof named pROCOS4/7-Stuffer1 which contains a DNA-Stuffer fragment for easier control of the double digest reaction can be used without any consequences regarding the final cloning results. Digestions are done according to the following protocols:

| buffer B + TX-100 (1X) | |
| --- | --- |
| Tris-HCl (pH 7.5) | 10 mM |
| MgCl$_2$ | 10 mM |
| BSA | 0.1 mg/ml |
| Triton X-100 | 0.02% |
| buffer A (1X) | |
| Tris-acetate (pH 7.9) | 33 mM |
| Mg-acetate | 10 mM |
| K-acetate | 66 mM |
| Dithiothreitol | 0.5 mM |

Vector DNA Digestion
1. For the restriction digestion of the vector DNA with KpnI set up the following mixture:
   pROCOS4/7-Stuffer1 x µl (200 µg)
   buffer B+TX-100 (10×) 150 µl
   BSA (10 mg/ml=100×) 15 µl
   KpnI X µl (400 U)
   ddH$_2$O to 1500 µl
      incubate at 37° C. for 3 hr and stop the reaction by incubating at 65° C. for 20 min.
2. Take an aliquot of 3 µl and run a 1% agarose gel with uncleaved DNA as a control.
3. Extract with phenol, precipitate with ethanol and resuspend the DNA in 820 µ TE-buffer.
4. Store a 20 µ aliquot of the digested DNA at −20° C. and mix the following for the digestion with SacI:
   pROCOS4/7-Stuffer/KpnI 800 µl
   buffer A (10×) 100 µl
   SacI X µl (400 U)
   ddH$_2$O 1000 µl
      incubate at 37° C. for 3 hr.
5. Take an aliquot of 3 µl and run a 1% agarose gel using uncleaved and single-cut DNA as a control.
6. Extract with phenol, precipitate with ethanol and resuspend the DNA in 550 µl TE-buffer.

Oligo DNA Digestion
1. For the digestion of double-stranded (ds) oligo DNA with KpnI set up the following four mixtures:
   NONA-CA, -CT, -GA or -GT dsDNA 100 µl
   buffer B+TX-100 (10×) 50 µl
   BSA (10 mg/ml=100×) 5 µl
   KpnI X µl (400 U)
   ddH$_2$O to 500 µl
   incubate at 37° C. for 5 hr.
   NOTE: Don't heat up the oligo DNA.
2. Take an aliquot of 5 µl and run a 4.5% agarose gel with uncleaved DNA as a control.
3. Extract with phenol, precipitate with ethanol and resuspend the DNA in 110 µl TE-buffer.
4. Store a 10 µl aliquot of the digested DNA at −20° C. and set up the following four mixtures for the digestion with SacI:
   NONA-CA, -GT, -GA or -GT/KpnI 100 µl
   buffer A (10×) 50 µl
   SacI X µl (400 U)
   ddH$_2$O to 500 µl
   incubate at 37° C. for 5 hr.
5. Take an aliquot of 5 µl and run a 4.5% agarose gel using uncleaved and single-cut DNA as a control.
6. Extract with phenol, precipitate with ethanol and resuspend the DNA in 55 µl TE-buffer.

The vector-DNA fragment may be purified using the following protocol:

Purification of Vector DNA Fragments by Gel Extraction
1. To separate the pROCOS4/7 vector DNA fragment from the stuffer fragment prepare a horizontal 1% agarose gel using a one-tooth combs.
2. Mix the DNA with 1/10 vol gel loading buffer, load onto the gel and electrophorese at 100 V until both fragments are clearly separated.
3. Put the gel on the UV transilluminator and excise the 5.5 kb pROCOS4/7 vector DNA fragment.
4. Extract the agarose slice using the JETsorb gel extraction kit (Genomed GmbH, Germany).

Vector- and insert DNA fragments are ligated and transformed according to the following protocols:

Ligation of DNA Fragments

Check the integrity of vector and insert DNA fragments by agarose gel electrophoresis (1% and 4.5% respectively). The concentration of the insert DNA may be estimated by comparing its ethidium bromide staining with standards of known quantity like assembled oligonucleotides. To determine the vector DNA concentration determine the absorbance at 260/280 nm.

T4 DNA ligase buffer (1×):
Tris-HCl (pH 7.5) 50 mM
MgCl$_2$ 10 mM
Dithiotreitol 10 mM
ATP 1 mM
BSA 25 µg/ml Test Ligation
1. To determine the appropriate ratio of insert to vector DNA a series of test ligations may be performed. For this assemble ligation reactions composed of:
   vector DNA fragment X µl (0.5 µg)
   T4 DNA ligase buffer (10×) 1 µl
   ddH$_2$O to 9 µl
2. Prepare three twofold dilutions of the insert DNAs in ddH$_2$O and add 1 µl of undiluted DNA as well as 1 µl of each dilution to one of the lgations reactions.

NOTE: The aim of this is to create vector to insert DNA (V/I) ratios of 1:5 to 2:1.
3. Add 1 unit T4 DNA ligase to each reaction and incubate overnight at 15° C.
   NOTE: As a control one reaction without insert DNA and one without ligase should be included.
4. Add 1 vol ddH$_2$O to each reaction and incubate at 65° C. for 10 min.
5. Precipitate the DNA with ethanol and resuspend it in 10 µl TE buffer.
6. Transform electrocompetent E. coli JM110λ cells with the content of each tube and plate dilutions on ampicillin containing LB agar plates.

Large-Scale Ligation
1. To create the libraries set up four of the following mixtures:
   vector DNA fragment X µl (¼ of the total prep.)
   insert DNA X µl (to create the optimal V/I-ratio)
   T4 DNA ligase buffer (10×) X µl (1/10 of the final vol)
   T4 DNA ligase X µl (2 U/µg DNA)
   ddH$_2$O to create a DNA conc. of 0.05 µg/µl
      incubate overnight at 15° C.
2. Extract with phenol, precipitate with ethanol and resuspend each of the ligation mixtures in sufficient TE-buffer to adjust the DNA concentration to 0.1–0.2 µg/µl.

Preparation of Competent Cells
1. Inoculate 20 ml of LB medium with a single colony of E. coli JM110λ and incubate at 37° C. and 180 rpm overnight.
2. Next day inoculate 2×1 liter of LB medium (2×2 l Erlenmeyer flask) at 1% with the overnight grown culture and incubate again at same conditions until an optical density of OD$_{600}$=0.6 has been reached.
3. Transfer 250 ml aliquots of the culture into centrifuge tubes (GS3), chill the cells on ice and centrifuge for 15 min at 8000 rpm and 4° C. (Sorvall RC5C centrifuge; GS3 rotor). Decant the supernatant.
4. Resuspend each pellet in 250 ml of ice-cold ddH$_2$O, centrifuge again (step 3) and decant the supernatant.
5. Resuspend each pellet in 125 ml of ice-cold ddH$_2$O, collect each of two aliquots in one tube, centrifuge again (step 3) and decant the supernatant.
6. Resuspend each pellet in 10 ml of ice-cold sterile glycerol (10%), collect all of the aliquots in one GSA centrifuge tube, centrifuge for 15 min at 8000 rpm and aspirate the supernatant.
7. Resuspend the bacterial pellet in 10 ml of ice-cold sterile glycerol (10%).
8. Fill aliquots of 100 µl in precooled, sterile Eppendorf reaction tubes, freeze immediately in liquid nitrogen and store at −70° C.

Transformation of E. coli Cells by Electroporation
1. Place frozen aliquots of competent E. coli cells on ice and let them thaw.
2. To each aliquot add up to 2 µg DNA in less than 10 µl and incubate on ice for 1 minute.
3. Fill the suspension in a prechilled electroporation cuvette (0.2 cm pathlength), place the cuvette in the electroporation sled and give a pulse at a voltage of 2.5 kV, a capacity of 25 µF and a resistance of 200 Ω (Gene Pulser and Puls Controller, Bio-Rad).
4. Immediately add 1 ml of LB medium (supplemented with 20 mM Glucose), mix and transfer the suspension in an Eppendorf reaction tube.
5. Incubate for 1 hour at 37° C. and plate on LB agar plates containing ampicillin (100 µg/ml). Incubate overnight at 37° C.

NOTE: To determine the size of the libraries also plate dilutions of the transformed cells.
6. To create library stocks resuspend the cells in LB/ampicillin medium, mix with 1 vol of sterile 87% glycerol and store at −70° C.

1b) Recombination

For recombination within the hypervariable sequences according to the four tube cosmix-plexing method the libraries can be preselected. For this purpose the *E. coli* cells containing the phagemid libraries are superinfected with M13K07 helper phages, progeny phages presenting fusion proteins are harvested and used for the first round of a panning according to standard methods e.g.:

Preparation of M13K07 Phage Stocks
PEG/NaCl-solution:
(16.7%/3.3 M)
  100 g PEG 8000
  116.9 g NaCl
  475 ml $H_2O$
PBS-buffer (1×):
  8.0 g NaCl
  0.2 g KCl
  1.43 g $Na_2HPO_4+2$ $H_2O$
  0.2 g $KH_2PO_4$
  $H_2O$ ad 1 l
  pH 6.8–7

1. Use a disposable pasteur pipette to pick a single, well separated M13K07 plaque from a *E. coli* WK6 lawn grown overnight on a LB/kanamycin (Km) plate, inoculate 20 ml of LB(2×)/Km medium (100 ml Erlenmeyer flask) with this agar slice and incubate overday at 37° C. on a shaker at 180 rpm.
2. Inoculate 2×500 ml LB(2×)/Km medium (in 2 l Erlenmeyer flasks) with 10 ml preculture and incubate overnight (37° C., 180 rpm).
3. Next day centrifuge four 250 ml aliquots for 15 minutes at 8000 rpm and 4° C. (Sorvall RC5C centrifuge; GS3 rotor). Transfer the supernatant into centrifuge bottles, centrifuge and transfer the supernatant again into fresh centrifuge bottles.
4. Add 0.15 vol. of PEG/NaCl solution, mix and incubate on ice for at least 2 hours.
5. Centrifuge for 60 min at 8000 rpm (GS3 rotor), decant the supernatant, centrifuge for some sec at up to 4000 rpm and remove last traces of the supernatant using a pipette.
6. Resuspend each PEG-pellet in 2.5 ml PBS solution and collect the resuspended phages in one SS34 centrifuge bottle. To clear the suspension centrifuge again for 10 min at 12000 rpm (SS34 rotor). Recover the supernatant (pipette), add $NaN_3$ to a final concentration of 0.02% and store the phages at 4° C.

Packaging of Phagemids (keep each library separate!)
1. Inoculate 100 ml of LB/Amp medium (1 l Erlenmeyer flask) with 1 ml of *E. coli* JM110λ cells containing phagemids (from overnight culture or resuspended cells) and incubate at 37° C. and 180 rpm until $OD_{600}$=0.5 (~2.5 h).
2. Add 500 μl M13K07 stock solution ($10^{11}$–$10^{12}$ cfu/ml), incubate at 37° C. for 15 min and continue shaking at 37° C. and 180 rpm overnight.
3. Next day centrifuge for 10 min at 8000 rpm (GSA rotor), decant the supernatant into a fresh bottle and repeat the centrifugation step.
4. Add 0.15 Vol of PEG/NaCl solution and incubate on ice for at least two hours.
5. Centrifuge for 60 min at 10000 rpm (GSA rotor), decant the supernatant and repeat the centrifugation and remove the supernatant completely.
6. Dissolve the pellet in 1 ml of PBS buffer and transfer the solution into an Eppendorf reaction tube. Centrifuge for 10 min at 13000 rpm (batch centrifuge), recover the cleared solution and add $NaN_3$ (final concentration of 0.02%). Store at 4° C.

Panning Procedure (keep each library separate!)
T-PBS solution:
  PBS-buffer containing 0.5% Tween 20
Blocking solution:
  PBS-buffer containing 2% skim milk powder
Elution-buffer:
  glycine (0.1 M; pH 2.2)

1. Coating of Microtiter Plates:
  Fill 100 μl of ligand solution (100 μg/ml PBS) into the wells of a 96-well microtiter plate (Nunc maxisorb) and incubate overnight at 4° C. or at least 2 hours at room temperature. Shake out the wells, slap the plate onto a paper towel and wash the wells once with T-PBS solution (ELISA plate washer or manually).
2. Blocking:
  Fill the wells with 400 μl of blocking solution and incubate at room temperature for ~1 hour. Shake out the wells, slap the plate onto a paper towel and wash the wells once with T-PBS.
3. Binding:
  Fill the coated and one uncoated well (as a control) with 100 μl of phage preparations diluted 1:1 with skim milk powder (usually ~$10^{10}$–$10^{11}$ phages/well) and incubate at room temperature for 1 to 3 hours.
4. Washing:
  Remove the solutions using a pipette and slap the plate onto a paper towel.
  In the first round of panning wash the wells once with T-PBS, incubate for 10 min with 400 μl blocking solution, wash again with T-PBS and finally two times with water. During all further rounds repeat the T-PBS washing steps three times. All washing steps can be carried out manually using a pipette or with an ELISA plate washer.
5. Elution:
  Slap out the plate and fill the wells with 100 μl of elution-buffer, incubate at room temperature for 15 min and transfer the solution into an Eppendorf reaction tube containing 6 μl Tris (2 M).
6. Determine the titer of eluted phages as described under 3.1.3.

Reinfection of *E. coli* Cells (keep each library separate!)
1. Mix the eluted phages and 10 ml of *E. coli* JM110λ log-phase cells and incubate for 30 min at 37° C.
2. Collect the cells by centrifugation (5 min, 8000 rpm, SS34 rotor) and resuspend the pellet in 400 μl of LB/Amp medium.
3. Plate each suspension on one LB/Amp agar plate (Ø 14.5 cm) and incubate overnight at 37° C.

After one round of panning populations of about $10^5$ individual clones enriched towards binding clones are expected. For recombination the phagemid DNA has to isolated according to standard protocols, e.g.:

Preparation of Phagemid-DNA from Reinfected Cells
1. Resuspend reinfected *E. coli* cells in 20 ml of LB/Amp medium and use of 200 μl for the inoculation of 3 ml LB/Amp medium.

2. Incubate at 180 rpm at 37° C. for 1 hour.
3. Prepare the DNA using Jetquick Plasmid Miniprep Spin Kits (Genomed GmbH, Germany) according to the instructions of the supplier.

Using this method up to 30 μg of DNA can be isolated. For pROCOS4/7 based libraries the phagemid size is 4.3 kb corresponding to a molecular weight of $2.9 \times 10^6$ g/mol or round about $2 \times 10^{11}$ phagemid molecules/μg DNA. Therefore 10 μg of recombined DNA contains more molecules than the theoretical number of different variants that can be created from $10^5$ clones $((10^5)^2 = 10^{10})$.

For recombination the phagemid DNA of each preselected library is cut separately e.g. with BpmI or alternatively with BsgI:

Digestion of the phagemid DNA
NEB3-buffer (1×)
NaCl 100 mM
Tris-HCl (pH 7.9) 50 mM
MgCl$_2$ 10 mM NONACOS-NGG:  BpiI  Bsg I 5' GGCTCTGATGGAAGACGT↓GCAGC(NNB)$_4$NGG(NNB)$_4$TGC↓TCCAGAGTCTTCCTC
                  ↑                                    BpmI ↑ BpiI NONACOS-NAM (SEQ ID NO:12):
    5' GGCTCTGATGGAAGACGTGCAGC(NNB)$_4$NAM(NNB)$_4$TGCTCCAGAGTCTTCCTC CTGTCG 3'
NONACOS-NTS (SEQ ID NO:13):
    5' GGCTCTGATGGAAGACGTGCAGC(NNB)$_4$NTS(NNB)$_4$TGCTCAGAGTCTTCCTC CTGTCG 3'
    where N means: A, C, G or T; B: C, G or T; M: A or C and S: C, G or T.

NONACOS-PCR-L (SEQ ID NO:14):
            BpiI    BsgI
5' GGCTCTGATGGAAGACGTGCAG 3'
NONACOS-PCR-R (SEQ ID NO:15):
            BpiI    BpmI
5' CGACAGGAGGAAGACTCTGGAG 3'

BpiI (GAAGAC), BsgI (GTGCAG) and BpmI (CTCCAG) restriction enzyme recognition sites are marked in bold type. BpiI cutting sites are marked by arrows.

Important vector DNA-sequences of pROCOS5/3 (SEQ ID NO:16):

BsgI          Eco47III
            5' GGCGAGCTCCCGT↓GCAGCGGTCTTCAGCGCTTGCCGTCTGACCGT
                              ↑ BpiI

Eco47III  BpiI                                    |pIII→
                AGCGCTGGAAGACGC↓TCCAGAGGGTACCCCGATATCAGAGCTGAA 3'
                                    BpmI ↑

Dithiothreitol 1 mM
1. Set up the following reaction
    phagemid-DNA 10 μg
    BpmI (2 μ/μl) 5 μl
    NEB3 (10×) 4 μl
    BSA (1 mg/ml) 4 μl
    H$_2$O up to 40 μl
    incubate at 37° C. for 5 hr.
2. Take an aliquots of 4 μl and run a 1% agarose gel to check the digestion.
3. Extract with phenol, precipitate with ethanol and resuspend the DNA in TE-buffer.

Digested phagemid-DNAs are religated at high concentration ($\geq 0.2$ μg/μl) to favour formation of concatemers, packaged into λ phage particles and used for the transfection of E. coli cells (according to "Packaging of Bacteriophage λ DNA in vitro; protocol I" p.2.100–2.104, in: Molecular Cloning—a Laboratory Manual, Sambrook et al. (eds.), 2. ed., 1989, Cold Spring Harbour Laboratory Press). Transfected phagemids are separated by packaging reinfection using M13K07 helper phages (see above).

EXAMPLE 2

Cosmix-plexing Using the One-tube-method
(According to Claims 11–17 and 44)

2a) Library Generation

Oligonucleotide sequences:

CTGTCG 3'
NONACOS-NCT (SEQ ID NO:11):
    5' GGCTCTGATGGAAGACGTGCAGC(NNB)$_4$NCT
    (NNB)$_4$TGCTCCAGAGTCTTCCTCC TGTCG 3'

BpiI (GAAGAC), BsgI (GTGCAG) Eco47III (AGCGCT) and BpmI (CTCCAG) restriction enzyme recognition sites are marked in bold type. BpiI cutting sites are marked by arrows. The first codon of the mature pIII-Protein (GAA) is also indicated.

To create libraries according to the one-tube method the hypervariable oligos NONACOS-NGG, -NCT, -NAM and -NTS are amplified using the PCR-primer NONACOS-R and NONACOS-L as described in example 1, except that the oligo-DNAs don't have to be kept separate.

After this pROCOS5/3-vector-DNA and double stranded (ds) oligo-DNA are digested with BpiI and ligated at the same time according to the following Protocol:

Digestion/Ligation

1. Set up the following mixture:

| | |
|---|---|
| pROCOS5/3 DNA | 200 μg |
| NONACOS-NGG, -NCT, -NAM and -NTS ds DNA | 100 μl |
| BpiI | 200 u |
| buffer G (10x) | 40 μl |
| BSA (10 mg/ml) | 4 μl |
| H$_2$O | up to 400 μl | incubate at 37° C. for 2 hr, add 200 units T4 DNA ligase and continue the incubation at 15 to 30° C. over night.

2. Take an aliquot of 3 μl and run a 1% agarose gel as a control.

This protocol favours the production of concatemers of the desired product, that can be packaged for example in *E. coli* JM110λ cells by λ-packaging according to example 1.

2b) Recombination

For panning and recombination the same methods as described for example 1 can be used, except that one library is used instead of four separate libraries.

What is claimed is:

1. A protein or peptide comprising a peptide sequence encoded by a DNA sequence from a bank of genes, wherein said genes comprise a double-stranded DNA sequence which is represented by the following formula of one of their strands:

$$5'B_1B_2B_3\ldots B_nX_{n+1}\ldots X_{n+a}Z_{n+a+1}Z_{n+a+2}X_{n+a+3}\ldots X_{n+a+b}Q_{n+a+b+1}\ldots Q_{n+a+b+j}3'$$

wherein n, a, b, and j are integers and are defined as: n>3, a>1, b>3 and j>1,
wherein $X_{n+1}\ldots X_{n+a+b}$ is a hypervariable sequence and B represents any of bases adenine (A), cytosine (C), guanine (G) or thymine (T), X represents any of bases A, C, G or T, Z represents any of bases A, C, G or T, and Q represents any of bases A, C, G or T, wherein,
(i) Z represents G or T at a G:T ratio of 1:1, and/or
(ii) Z represents C or T at a C:T ratio of 1:1, and/or
(iii) Z represents A or G at a A:G ratio of 1:1, and/or
(iv) Z represents A or C at a A:C ratio of 1:1, and wherein
subsequences $B_1\ldots B_n$ and/or $Q_{n+a+b+1}\ldots Q_{n+a+b+j}$ represent recognition sites for restriction enzymes, and wherein the recognition sites are oriented such that their cleavage site upon cleavage generates a cohesive end including the two bases designated Z.

2. A peptide or protein according to claim 1 wherein each gene is provided as a display vector, especially as M13 phage or M13 like phage or a phagemid.

3. A peptide or protein according to claim 1, wherein said set of four gene banks are characterized as follows:

a first gene bank in which Z represents G or T;
a second gene bank in which Z represents C or T;
a third gene bank in which Z represents A or G; and
a fourth gene bank in which Z represents A or C.

4. A protein or peptide according to claim 3, wherein each gene is provided as display vector.

5. A protein or peptide comprising a peptide sequence encoded by a DNA sequence from a bank of genes, wherein said genes comprise a double stranded DNA sequence which is represented by the following formula of one of their strands:

$$5'B_1B_2B_3\ldots B_nX_{n+1}\ldots X_{n+a}Z_{n+a+1}Z_{n+a+2}X_{n+a+3}\ldots X_{n+a+b}Q_{n+a+b+1}\ldots Q_{n+a+b+j}3'$$

wherein n, a, b and j are integers and
n>3, a>1, b >3 and j>1,
wherein $X_{n+1}\ldots X_{n+a+b}$ is a hypervariable sequence and B represents any one of bases A, C, G or T, X represents any one of bases A, C, G or T, Z represents any one of bases A, C, G or T, and Q represents any one of bases A, C, G or T, and wherein
four set of oligonucleotide sequences comprising $Z_{n+a+1}$ and $Z_{n+a+2}$ are present, wherein the four sets are characterized as follows:
(i) a first set in which $Z_{n+a+1}$ represents G and $Z_{n+a+2}$ also represents G;
(ii) a second set in which $Z_{n+a+1}$ represents C and $Z_{n+a+2}$ represents T;
(iii) a third set in which $Z_{n+a+1}$ represents A and $Z_{n+a+2}$ represents A or C, and
(iv) a fourth set: $Z_{n+a+1}$ represents T and $Z_{n+a+2}$ represents C or G, and wherein sequences $B_1 \ldots B_n$ and/or $Q_{n+a+b+1} \ldots Q_{n+a+b+j}$ represent recognition sites for restriction enzymes, wherein the recognition sites are oriented such that their cleavage site upon cleavage generates a cohesive end including the two bases designated Z.

6. A protein or peptide according to claim 5, wherein the four sets of oligonucleotide sequences are present at a ratio of (i):(ii):(iii):(iv) of (0 to 1):(0 to 1):(0 to 1):(0 to 1) with the proviso that at least one of said sets is present.

7. A peptide or protein according to claim 5 or 6, wherein subsequences $B_1 \ldots B_n$ and/or $Q_{n+a+b+1} \ldots Q_{n+a+b+j}$ represent recognition sites for restriction enzymes, and wherein the recognition sites are oriented such that their cleavage site upon cleavage generates a cohesive end including the two bases designated Z.

8. A protein or peptide comprising a peptide sequence encoded by a DNA sequence from a bank of genes wherein said genes comprise a double stranded DNA sequence which is represented by the following formula of one of their strands:

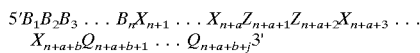

wherein n, a, b and j are integers and
n>3, a>1, b>3 and j>1,
wherein $X_{n+1} \ldots X_{n+a+b}$ is a hypervariable sequence and B represents any one of bases A, C, G or T, X represents any one of bases A, C, G or T, Z represents any one of bases A, C, G or T, and Q represents any one of bases A, C, G or T, and wherein
the following six sets of oligonucleotide sequences comprising $X_{n+a}$, $Z_{n+a+1}$ and $Z_{n+a+2}$ are present, wherein the six sets are characterized as follows:
(i) a first set in which $X_{n+a}$ represents A, G and/or T, or $X_{n+a}$ represents C, G and/or T, $Z_{n+a+1}$ represents G and $Z_{n+a+2}$ represents G;
(ii) a second set in which $X_{n+a}$ represents A, C, G and/or T, $Z_{n+a+1}$ represents C and $Z_{n+a+2}$ represents T;
(iii) a third set in which $X_{n+a}$ represents A, C and/or G, $Z_{n+a+1}$ represents A and $Z_{n+a+2}$ represents A;
(iv) a fourth set in which $X_{n+a}$ represents A, C, G and/or T, $Z_{n+a+1}$ represents A and $Z_{n+a+2}$ represents C;
(v) a fifth set in which $X_{n+a}$ represents A, C, G and/or T, $Z_{n+a+1}$ represents T and $Z_{n+a+2}$ represents C;
(vi) a sixth set in which $X_{n+a}$ represents A, $Z_{n+a+1}$ represents T and $Z_{n+a+2}$ represents G.
wherein $B_1 \ldots B_n$ and/or $Q_{n+a+b+1} \ldots Q_{n+a+b+j}$ represent recognition sites for restriction enzymes and wherein the recognition sites are oriented such that their cleavage site upon cleavage generates a cohesive end including the two bases designated Z.

9. A protein or peptide according to claim 8, wherein the six sets of oligonucleotide sequences are present at a ratio of (i):(ii):(iii):(iv):(v):(vi) of (0 to 1):(0 to 1):(0 to 1):(0 to 1):(0 to 1) with the proviso that at least one of said sets is present.

10. A protein or peptide according to claim 8, wherein each gene is provided as display vector.

11. A protein or peptide according to claim 1, characterized in that n=j=6, a=14 and b=16.

12. A protein or peptide according to claim 1, wherein the restriction enzyme is a type II S restriction enzyme.

13. A protein or peptide according to claim 1, wherein the gene sequence is characterized in that:
(a) subsequence $B_1 \ldots B_n$ is the recognition site for the restriction enzyme BpmI (CTGGAG) and $Q_{n+a+b+1} \ldots Q_{n+a+b+j}$ is an inverted BsgI recognition site (CTGGCAG); or
(b) subsequence $B_1 \ldots B_n$ is the recognition site for the restriction enzyme BsgI recognition site (CTGGCAG) and $Q_{n+a+b+1} \ldots Q_{n+a+b+j}$ is an inverted BpmI (CTGGAG).

14. A protein or peptide according to claim 1, wherein the gene sequence is characterized in that the hypervariable sequence $X_{n+1} \ldots X_{n+a+b}$ contains NNB or NNK wherein
N=adenine (A), cytosine (C) guanine (G) or thymine(T);
B=cytosine (C), guanine (G) or thymine (T); and
K=guanine (G) or thymine (T).

* * * * *

UNITED STATES PATENT AND TRADEMARK OFFICE
CERTIFICATE OF CORRECTION

PATENT NO.    : 6,640,192 B1
DATED         : October 28, 2003
INVENTOR(S)   : Collins et al.

It is certified that error appears in the above-identified patent and that said Letters Patent is hereby corrected as shown below:

<u>Column 76,</u>
Line 19, before "with" insert -- (0 to 1) --.

Signed and Sealed this

Twenty-third Day of March, 2004

JON W. DUDAS
*Acting Director of the United States Patent and Trademark Office*

SEQUENCE LISTING (1) GENERAL INFORMATION:

(iii) NUMBER OF SEQUENCES: 18

(2) INFORMATION FOR SEQ ID NO: 1:

(i) SEQUENCE CHARACTERISTICS:
      (A) LENGTH: 62 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "hypervariable DNA oligo"

(ix) FEATURE:
      (A) NAME/KEY: misc_feature
      (B) LOCATION:18
      (D) OTHER INFORMATION:/note= "V = A or C or G"

(ix) FEATURE:
      (A) NAME/KEY: misc_feature
      (B) LOCATION:21
      (D) OTHER INFORMATION:/note= "V = A or C or G"

(ix) FEATURE:
      (A) NAME/KEY: misc_feature
      (B) LOCATION:19
      (D) OTHER INFORMATION:/note= "N can be A, C, G or T"

(ix) FEATURE:
      (A) NAME/KEY: misc_feature
      (B) LOCATION:20
      (D) OTHER INFORMATION:/note= "N can be A, C, G or T"

(ix) FEATURE:
      (A) NAME/KEY: misc_feature
      (B) LOCATION:22
      (D) OTHER INFORMATION:/note= "N can be A, C, G or T"

(ix) FEATURE:
      (A) NAME/KEY: misc_feature
      (B) LOCATION:23
      (D) OTHER INFORMATION:/note= "N can be A, C, G or T"

(ix) FEATURE:
      (A) NAME/KEY: misc_feature
      (B) LOCATION:24
      (D) OTHER INFORMATION:/note= "V = A or C or G"

(ix) FEATURE:
      (A) NAME/KEY: misc_feature
      (B) LOCATION:25
      (D) OTHER INFORMATION:/note= "N can be A, C, G or T"

-continued

```
(ix) FEATURE:
     (A) NAME/KEY: misc_feature
     (B) LOCATION:26
     (D) OTHER INFORMATION:/note= "N can be A, C, G or T"

(ix) FEATURE:
     (A) NAME/KEY: misc_feature
     (B) LOCATION:27
     (D) OTHER INFORMATION:/note= "V = A or C or G"

(ix) FEATURE:
     (A) NAME/KEY: misc_feature
     (B) LOCATION:28
     (D) OTHER INFORMATION:/note= "N can be A, C, G or T"

(ix) FEATURE:
     (A) NAME/KEY: misc_feature
     (B) LOCATION:29
     (D) OTHER INFORMATION:/note= "N can be A, C, G or T"

(ix) FEATURE:
     (A) NAME/KEY: misc_feature
     (B) LOCATION:30
     (D) OTHER INFORMATION:/note= "K can be G or T"

(ix) FEATURE:
     (A) NAME/KEY: misc_feature
     (B) LOCATION:31
     (D) OTHER INFORMATION:/note= "K can be G or T"

(ix) FEATURE:
     (A) NAME/KEY: misc_feature
     (B) LOCATION:32
     (D) OTHER INFORMATION:/note= "N can be A, C, G or T"

(ix) FEATURE:
     (A) NAME/KEY: misc_feature
     (B) LOCATION:33
     (D) OTHER INFORMATION:/note= "V = A or C or G"

(ix) FEATURE:
     (A) NAME/KEY: misc_feature
     (B) LOCATION:34
     (D) OTHER INFORMATION:/note= "N can be A, C, G or T"

(ix) FEATURE:
     (A) NAME/KEY: misc_feature
     (B) LOCATION:35
     (D) OTHER INFORMATION:/note= "N can be A, C, G or T"

(ix) FEATURE:
     (A) NAME/KEY: misc_feature
     (B) LOCATION:36
     (D) OTHER INFORMATION:/note= "V = A or C or G"

(ix) FEATURE:
     (A) NAME/KEY: misc_feature
     (B) LOCATION:37
     (D) OTHER INFORMATION:/note= "N can be A, C, G or T"

(ix) FEATURE:
     (A) NAME/KEY: misc_feature
     (B) LOCATION:38
     (D) OTHER INFORMATION:/note= "N can be A, C, G or T"

(ix) FEATURE:
     (A) NAME/KEY: misc_feature
     (B) LOCATION:39
     (D) OTHER INFORMATION:/note= "V = A or C or G"

(ix) FEATURE:
     (A) NAME/KEY: misc_feature
     (B) LOCATION:40
     (D) OTHER INFORMATION:/note= "N can be A, C, G or T"
```

```
    (ix) FEATURE:
          (A) NAME/KEY: misc_feature
          (B) LOCATION:41
          (D) OTHER INFORMATION:/note= "N can be A, C, G or T"

(ix) FEATURE:
          (A) NAME/KEY: misc_feature
          (B) LOCATION:42
          (D) OTHER INFORMATION:/note= "V = A or C or G"

(ix) FEATURE:
          (A) NAME/KEY: misc_feature
          (B) LOCATION:43
          (D) OTHER INFORMATION:/note= "N can be A, C, G or T"

(ix) FEATURE:
          (A) NAME/KEY: misc_feature
          (B) LOCATION:44
          (D) OTHER INFORMATION:/note= "N can be A, C, G or T"

(xi) SEQUENCE DESCRIPTION: SEQ ID NO: 1:

TCGGGGTACC TGGAGCAVNN VNNVNNVNNK KNVNNVNNVN NVNNGCTGCA CGGGAGCTCG     60

CC                                                                  62

(2) INFORMATION FOR SEQ ID NO: 2:

(i) SEQUENCE CHARACTERISTICS:
          (A) LENGTH: 62 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "hypervariable DNA oligo"

(ix) FEATURE:
          (A) NAME/KEY: misc_feature
          (B) LOCATION:18
          (D) OTHER INFORMATION:/note= "V = A or C or G"

(ix) FEATURE:
          (A) NAME/KEY: misc_feature
          (B) LOCATION:19
          (D) OTHER INFORMATION:/note= "N can be A, C, G or T"

(ix) FEATURE:
          (A) NAME/KEY: misc_feature
          (B) LOCATION:20
          (D) OTHER INFORMATION:/note= "N can be A, C, G or T"

(ix) FEATURE:
          (A) NAME/KEY: misc_feature
          (B) LOCATION:21
          (D) OTHER INFORMATION:/note= "V = A or C or G"

(ix) FEATURE:
          (A) NAME/KEY: misc_feature
          (B) LOCATION:22
          (D) OTHER INFORMATION:/note= "N can be A, C, G or T"

(ix) FEATURE:
          (A) NAME/KEY: misc_feature
          (B) LOCATION:23
          (D) OTHER INFORMATION:/note= "N can be A, C, G or T"

(ix) FEATURE:
          (A) NAME/KEY: misc_feature
          (B) LOCATION:24
          (D) OTHER INFORMATION:/note= "V = A or C or G"

(ix) FEATURE:
          (A) NAME/KEY: misc_feature
          (B) LOCATION:25
          (D) OTHER INFORMATION:/note= "N can be A, C, G or T"
```

-continued

```
(ix) FEATURE:
    (A) NAME/KEY: misc_feature
    (B) LOCATION:26
    (D) OTHER INFORMATION:/note= "N can be A, C, G or T"

(ix) FEATURE:
    (A) NAME/KEY: misc_feature
    (B) LOCATION:27
    (D) OTHER INFORMATION:/note= "V = A or C or G"

(ix) FEATURE:
    (A) NAME/KEY: misc_feature
    (B) LOCATION:28
    (D) OTHER INFORMATION:/note= "N can be A, C, G or T"

(ix) FEATURE:
    (A) NAME/KEY: misc_feature
    (B) LOCATION:29
    (D) OTHER INFORMATION:/note= "N can be A, C, G or T"

(ix) FEATURE:
    (A) NAME/KEY: misc_feature
    (B) LOCATION:30
    (D) OTHER INFORMATION:/note= "R can be G or A"

(ix) FEATURE:
    (A) NAME/KEY: misc_feature
    (B) LOCATION:31
    (D) OTHER INFORMATION:/note= "R can be G or A"

(ix) FEATURE:
    (A) NAME/KEY: misc_feature
    (B) LOCATION:32
    (D) OTHER INFORMATION:/note= "N can be A, C, G or T"

(ix) FEATURE:
    (A) NAME/KEY: misc_feature
    (B) LOCATION:33
    (D) OTHER INFORMATION:/note= "V = A or C or G"

(ix) FEATURE:
    (A) NAME/KEY: misc_feature
    (B) LOCATION:34
    (D) OTHER INFORMATION:/note= "N can be A, C, G or T"

(ix) FEATURE:
    (A) NAME/KEY: misc_feature
    (B) LOCATION:35
    (D) OTHER INFORMATION:/note= "N can be A, C, G or T"

(ix) FEATURE:
    (A) NAME/KEY: misc_feature
    (B) LOCATION:36
    (D) OTHER INFORMATION:/note= "V = A or C or G"

(ix) FEATURE:
    (A) NAME/KEY: misc_feature
    (B) LOCATION:37
    (D) OTHER INFORMATION:/note= "N can be A, C, G or T"

(ix) FEATURE:
    (A) NAME/KEY: misc_feature
    (B) LOCATION:38
    (D) OTHER INFORMATION:/note= "N can be A, C, G or T"

(ix) FEATURE:
    (A) NAME/KEY: misc_feature
    (B) LOCATION:39
    (D) OTHER INFORMATION:/note= "V = A or C or G"

(ix) FEATURE:
    (A) NAME/KEY: misc_feature
    (B) LOCATION:40
    (D) OTHER INFORMATION:/note= "N can be A, C, G or T"

(ix) FEATURE:
    (A) NAME/KEY: misc_feature
    (B) LOCATION:41
    (D) OTHER INFORMATION:/note= "N can be A, C, G or T"
```

(ix) FEATURE:
         (A) NAME/KEY: misc_feature
         (B) LOCATION:42
         (D) OTHER INFORMATION:/note= "V = A or C or G"

(ix) FEATURE:
         (A) NAME/KEY: misc_feature
         (B) LOCATION:43
         (D) OTHER INFORMATION:/note= "N can be A, C, G or T"

(ix) FEATURE:
         (A) NAME/KEY: misc_feature
         (B) LOCATION:44
         (D) OTHER INFORMATION:/note= "N can be A, C, G or T"

(xi) SEQUENCE DESCRIPTION: SEQ ID NO: 2:

TCGGGGTACC TGGAGCAVNN VNNVNNVNNR RNVNNVNNVN NVNNGCTGCA CGGGAGCTCG    60

CC                                                                  62

(2) INFORMATION FOR SEQ ID NO: 3:

(i) SEQUENCE CHARACTERISTICS:
         (A) LENGTH: 62 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "hypervariable DNA oligo"

(ix) FEATURE:
         (A) NAME/KEY: misc_feature
         (B) LOCATION:18
         (D) OTHER INFORMATION:/note= "V = A or C or G"

(ix) FEATURE:
         (A) NAME/KEY: misc_feature
         (B) LOCATION:19
         (D) OTHER INFORMATION:/note= "N can be A, C, G or T"

(ix) FEATURE:
         (A) NAME/KEY: misc_feature
         (B) LOCATION:20
         (D) OTHER INFORMATION:/note= "N can be A, C, G or T"

(ix) FEATURE:
         (A) NAME/KEY: misc_feature
         (B) LOCATION:21
         (D) OTHER INFORMATION:/note= "V = A or C or G"

(ix) FEATURE:
         (A) NAME/KEY: misc_feature
         (B) LOCATION:22
         (D) OTHER INFORMATION:/note= "N can be A, C, G or T"

(ix) FEATURE:
         (A) NAME/KEY: misc_feature
         (B) LOCATION:23
         (D) OTHER INFORMATION:/note= "N can be A, C, G or T"

(ix) FEATURE:
         (A) NAME/KEY: misc_feature
         (B) LOCATION:24
         (D) OTHER INFORMATION:/note= "V = A or C or G"

(ix) FEATURE:
         (A) NAME/KEY: misc_feature
         (B) LOCATION:25
         (D) OTHER INFORMATION:/note= "N can be A, C, G or T"

(ix) FEATURE:
         (A) NAME/KEY: misc_feature
         (B) LOCATION:26
         (D) OTHER INFORMATION:/note= "N can be A, C, G or T"

```
    (ix) FEATURE:
        (A) NAME/KEY: misc_feature
        (B) LOCATION:27
        (D) OTHER INFORMATION:/note= "V = A or C or G"

(ix) FEATURE:
        (A) NAME/KEY: misc_feature
        (B) LOCATION:28
        (D) OTHER INFORMATION:/note= "N can be A, C, G or T"

(ix) FEATURE:
        (A) NAME/KEY: misc_feature
        (B) LOCATION:29
        (D) OTHER INFORMATION:/note= "N can be A, C, G or T"

(ix) FEATURE:
        (A) NAME/KEY: misc_feature
        (B) LOCATION:30
        (D) OTHER INFORMATION:/note= "Y = C or T"

(ix) FEATURE:
        (A) NAME/KEY: misc_feature
        (B) LOCATION:31
        (D) OTHER INFORMATION:/note= "Y = C or T"

(ix) FEATURE:
        (A) NAME/KEY: misc_feature
        (B) LOCATION:32
        (D) OTHER INFORMATION:/note= "N can be A, C, G or T"

(ix) FEATURE:
        (A) NAME/KEY: misc_feature
        (B) LOCATION:33
        (D) OTHER INFORMATION:/note= "V = A or C or G"

(ix) FEATURE:
        (A) NAME/KEY: misc_feature
        (B) LOCATION:34
        (D) OTHER INFORMATION:/note= "N can be A, C, G or T"

(ix) FEATURE:
        (A) NAME/KEY: misc_feature
        (B) LOCATION:35
        (D) OTHER INFORMATION:/note= "N can be A, C, G or T"

(ix) FEATURE:
        (A) NAME/KEY: misc_feature
        (B) LOCATION:36
        (D) OTHER INFORMATION:/note= "V = A or C or G"

(ix) FEATURE:
        (A) NAME/KEY: misc_feature
        (B) LOCATION:37
        (D) OTHER INFORMATION:/note= "N can be A, C, G or T"

(ix) FEATURE:
        (A) NAME/KEY: misc_feature
        (B) LOCATION:38
        (D) OTHER INFORMATION:/note= "N can be A, C, G or T"

(ix) FEATURE:
        (A) NAME/KEY: misc_feature
        (B) LOCATION:39
        (D) OTHER INFORMATION:/note= "V = A or C or G"

(ix) FEATURE:
        (A) NAME/KEY: misc_feature
        (B) LOCATION:40
        (D) OTHER INFORMATION:/note= "N can be A, C, G or T"

(ix) FEATURE:
        (A) NAME/KEY: misc_feature
        (B) LOCATION:41
        (D) OTHER INFORMATION:/note= "N can be A, C, G or T"

(ix) FEATURE:
        (A) NAME/KEY: misc_feature
        (B) LOCATION:42
        (D) OTHER INFORMATION:/note= "V = A or C or G"
```

```
    (ix) FEATURE:
         (A) NAME/KEY: misc_feature
         (B) LOCATION:43
         (D) OTHER INFORMATION:/note= "N can be A, C, G or T"

(ix) FEATURE:
         (A) NAME/KEY: misc_feature
         (B) LOCATION:44
         (D) OTHER INFORMATION:/note= "N can be A, C, G or T"

(xi) SEQUENCE DESCRIPTION: SEQ ID NO: 3:

TCGGGGTACC TGGAGCAVNN VNNVNNVNNY YNVNNVNNVN NVNNGCTGCA CGGGAGCTCG        60

CC                                                                      62

(2) INFORMATION FOR SEQ ID NO: 4:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "hypervariable DNA oligo"

(ix) FEATURE:
         (A) NAME/KEY: misc_feature
         (B) LOCATION:18
         (D) OTHER INFORMATION:/note= "V = A or C or G"

(ix) FEATURE:
         (A) NAME/KEY: misc_feature
         (B) LOCATION:19
         (D) OTHER INFORMATION:/note= "N can be A, C, G or T"

(ix) FEATURE:
         (A) NAME/KEY: misc_feature
         (B) LOCATION:20
         (D) OTHER INFORMATION:/note= "N can be A, C, G or T"

(ix) FEATURE:
         (A) NAME/KEY: misc_feature
         (B) LOCATION:21
         (D) OTHER INFORMATION:/note= "V = A or C or G"

(ix) FEATURE:
         (A) NAME/KEY: misc_feature
         (B) LOCATION:22
         (D) OTHER INFORMATION:/note= "N can be A, C, G or T"

(ix) FEATURE:
         (A) NAME/KEY: misc_feature
         (B) LOCATION:23
         (D) OTHER INFORMATION:/note= "N can be A, C, G or T"

(ix) FEATURE:
         (A) NAME/KEY: misc_feature
         (B) LOCATION:24
         (D) OTHER INFORMATION:/note= "V = A or C or G"

(ix) FEATURE:
         (A) NAME/KEY: misc_feature
         (B) LOCATION:25
         (D) OTHER INFORMATION:/note= "N can be A, C, G or T"

(ix) FEATURE:
         (A) NAME/KEY: misc_feature
         (B) LOCATION:26
         (D) OTHER INFORMATION:/note= "N can be A, C, G or T"

(ix) FEATURE:
         (A) NAME/KEY: misc_feature
         (B) LOCATION:27
         (D) OTHER INFORMATION:/note= "V = A or C or G"
```

```
-continued (ix) FEATURE:
     (A) NAME/KEY: misc_feature
     (B) LOCATION:28
     (D) OTHER INFORMATION:/note= "N can be A, C, G or T"

(ix) FEATURE:
     (A) NAME/KEY: misc_feature
     (B) LOCATION:29
     (D) OTHER INFORMATION:/note= "N can be A, C, G or T"

(ix) FEATURE:
     (A) NAME/KEY: misc_feature
     (B) LOCATION:30
     (D) OTHER INFORMATION:/note= "M = A or C"

(ix) FEATURE:
     (A) NAME/KEY: misc_feature
     (B) LOCATION:31
     (D) OTHER INFORMATION:/note= "M = A or C"

(ix) FEATURE:
     (A) NAME/KEY: misc_feature
     (B) LOCATION:32
     (D) OTHER INFORMATION:/note= "N can be A, C, G or T"

(ix) FEATURE:
     (A) NAME/KEY: misc_feature
     (B) LOCATION:33
     (D) OTHER INFORMATION:/note= "V = A or C or G"

(ix) FEATURE:
     (A) NAME/KEY: misc_feature
     (B) LOCATION:34
     (D) OTHER INFORMATION:/note= "N can be A, C, G or T"

(ix) FEATURE:
     (A) NAME/KEY: misc_feature
     (B) LOCATION:35
     (D) OTHER INFORMATION:/note= "N can be A, C, G or T"

(ix) FEATURE:
     (A) NAME/KEY: misc_feature
     (B) LOCATION:36
     (D) OTHER INFORMATION:/note= "V = A or C or G"

(ix) FEATURE:
     (A) NAME/KEY: misc_feature
     (B) LOCATION:37
     (D) OTHER INFORMATION:/note= "N can be A, C, G or T"

(ix) FEATURE:
     (A) NAME/KEY: misc_feature
     (B) LOCATION:38
     (D) OTHER INFORMATION:/note= "N can be A, C, G or T"

(ix) FEATURE:
     (A) NAME/KEY: misc_feature
     (B) LOCATION:39
     (D) OTHER INFORMATION:/note= "V = A or C or G"

(ix) FEATURE:
     (A) NAME/KEY: misc_feature
     (B) LOCATION:40
     (D) OTHER INFORMATION:/note= "N can be A, C, G or T"

(ix) FEATURE:
     (A) NAME/KEY: misc_feature
     (B) LOCATION:41
     (D) OTHER INFORMATION:/note= "N can be A, C, G or T"

(ix) FEATURE:
     (A) NAME/KEY: misc_feature
     (B) LOCATION:42
     (D) OTHER INFORMATION:/note= "V = A or C or G"

(ix) FEATURE:
     (A) NAME/KEY: misc_feature
     (B) LOCATION:43
     (D) OTHER INFORMATION:/note= "N can be A, C, G or T"
```

(ix) FEATURE:
    (A) NAME/KEY: misc_feature
    (B) LOCATION:44
    (D) OTHER INFORMATION:/note= "N can be A, C, G or T"

(xi) SEQUENCE DESCRIPTION: SEQ ID NO: 4:

TCGGGGTACC TGGAGCAVNN VNNVNNVNNM MNVNNVNNVN NVNNGCTGCA CGGGAGCTCG    60

CC    62

(2) INFORMATION FOR SEQ ID NO: 5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA oligo"

(xi) SEQUENCE DESCRIPTION: SEQ ID NO: 5:

GGCGAGCTCC CGTGCAGC    18

(2) INFORMATION FOR SEQ ID NO: 6:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA oligo"

(xi) SEQUENCE DESCRIPTION: SEQ ID NO: 6:

TCGGGGTACC TGGAGCA    17

(2) INFORMATION FOR SEQ ID NO: 7:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "vector DNA-Sequence"

(xi) SEQUENCE DESCRIPTION: SEQ ID NO: 7:

GGCGAGCTCC CGTGCAGCGC TCCAGGTACC CCGATATCAG AGCTGAA    47

(2) INFORMATION FOR SEQ ID NO: 8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "pROCOS4/7-Stuffer 1"

(xi) SEQUENCE DESCRIPTION: SEQ ID NO: 8:

GGCGAGCTCC CGTGCAGCGC T    21

(2) INFORMATION FOR SEQ ID NO: 9:

```
        (i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = " pROCOS4/7-Stuffer 1"

(xi) SEQUENCE DESCRIPTION: SEQ ID NO: 9:

AGCGCTCCAG GTACCCCGAT ATCAGAGCTG AA                                              32

(2) INFORMATION FOR SEQ ID NO: 10:

(i) SEQUENCE CHARACTERISTICS:
            (A) LENGTH: 74 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "hypervariable DNA oligo"

(ix) FEATURE:
            (A) NAME/KEY: misc_feature
            (B) LOCATION:24
            (D) OTHER INFORMATION:/note= "N = A or C or G or T"

(ix) FEATURE:
            (A) NAME/KEY: misc_feature
            (B) LOCATION:25
            (D) OTHER INFORMATION:/note= "N = A or C or G or T"

(ix) FEATURE:
            (A) NAME/KEY: misc_feature
            (B) LOCATION:26
            (D) OTHER INFORMATION:/note= "B = C or G or T"

(ix) FEATURE:
            (A) NAME/KEY: misc_feature
            (B) LOCATION:27
            (D) OTHER INFORMATION:/note= "N = A or C or G or T"

(ix) FEATURE:
            (A) NAME/KEY: misc_feature
            (B) LOCATION:28
            (D) OTHER INFORMATION:/note= "N = A or C or G or T"

(ix) FEATURE:
            (A) NAME/KEY: misc_feature
            (B) LOCATION:29
            (D) OTHER INFORMATION:/note= "B = C or G or T"

(ix) FEATURE:
            (A) NAME/KEY: misc_feature
            (B) LOCATION:30
            (D) OTHER INFORMATION:/note= "N = A or C or G or T"

(ix) FEATURE:
            (A) NAME/KEY: misc_feature
            (B) LOCATION:31
            (D) OTHER INFORMATION:/note= "N = A or C or G or T"

(ix) FEATURE:
            (A) NAME/KEY: misc_feature
            (B) LOCATION:32
            (D) OTHER INFORMATION:/note= "B = C or G or T"

(ix) FEATURE:
            (A) NAME/KEY: misc_feature
            (B) LOCATION:33
            (D) OTHER INFORMATION:/note= "N = A or C or G or T"

(ix) FEATURE:
            (A) NAME/KEY: misc_feature
            (B) LOCATION:34
            (D) OTHER INFORMATION:/note= "N = A or C or G or T"
```

(ix) FEATURE:
    (A) NAME/KEY: misc_feature
    (B) LOCATION:35
    (D) OTHER INFORMATION:/note= "B = C or G or T"

(ix) FEATURE:
    (A) NAME/KEY: misc_feature
    (B) LOCATION:36
    (D) OTHER INFORMATION:/note= "N = A or C or G or T"

(ix) FEATURE:
    (A) NAME/KEY: misc_feature
    (B) LOCATION:39
    (D) OTHER INFORMATION:/note= "N = A or C or G or T"

(ix) FEATURE:
    (A) NAME/KEY: misc_feature
    (B) LOCATION:40
    (D) OTHER INFORMATION:/note= "N = A or C or G or T"

(ix) FEATURE:
    (A) NAME/KEY: misc_feature
    (B) LOCATION:41
    (D) OTHER INFORMATION:/note= "B = C or G or T"

(ix) FEATURE:
    (A) NAME/KEY: misc_feature
    (B) LOCATION:42
    (D) OTHER INFORMATION:/note= "N = A or C or G or T"

(ix) FEATURE:
    (A) NAME/KEY: misc_feature
    (B) LOCATION:43
    (D) OTHER INFORMATION:/note= "N = A or C or G or T"

(ix) FEATURE:
    (A) NAME/KEY: misc_feature
    (B) LOCATION:44
    (D) OTHER INFORMATION:/note= "B = C or G or T"

(ix) FEATURE:
    (A) NAME/KEY: misc_feature
    (B) LOCATION:45
    (D) OTHER INFORMATION:/note= "N = A or C or G or T"

(ix) FEATURE:
    (A) NAME/KEY: misc_feature
    (B) LOCATION:46
    (D) OTHER INFORMATION:/note= "N = A or C or G or T"

(ix) FEATURE:
    (A) NAME/KEY: misc_feature
    (B) LOCATION:47
    (D) OTHER INFORMATION:/note= "B = C or G or T"

(ix) FEATURE:
    (A) NAME/KEY: misc_feature
    (B) LOCATION:48
    (D) OTHER INFORMATION:/note= "N = A or C or G or T"

(ix) FEATURE:
    (A) NAME/KEY: misc_feature
    (B) LOCATION:49
    (D) OTHER INFORMATION:/note= "N = A or C or G or T"

(ix) FEATURE:
    (A) NAME/KEY: misc_feature
    (B) LOCATION:50
    (D) OTHER INFORMATION:/note= "B = C or G or T"

(xi) SEQUENCE DESCRIPTION: SEQ ID NO: 10:

GGCTCTGATG GAAGACGTGC AGCNNBNNBN NBNNBNGGNN BNNBNNBNNB TGCTCCAGAG    60

TCTTCCTCCT GTCG    74

(2) INFORMATION FOR SEQ ID NO: 11:

(i) SEQUENCE CHARACTERISTICS:
    (A) LENGTH: 74 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "hypervariable DNA oligo"

(ix) FEATURE:
    (A) NAME/KEY: misc_feature
    (B) LOCATION:24
    (D) OTHER INFORMATION:/note= "N = A or C or G or T"

(ix) FEATURE:
    (A) NAME/KEY: misc_feature
    (B) LOCATION:25
    (D) OTHER INFORMATION:/note= "N = A or C or G or T"

(ix) FEATURE:
    (A) NAME/KEY: misc_feature
    (B) LOCATION:26
    (D) OTHER INFORMATION:/note= "B = C or G or T"

(ix) FEATURE:
    (A) NAME/KEY: misc_feature
    (B) LOCATION:27
    (D) OTHER INFORMATION:/note= "N = A or C or G or T"

(ix) FEATURE:
    (A) NAME/KEY: misc_feature
    (B) LOCATION:28
    (D) OTHER INFORMATION:/note= "N = A or C or G or T"

(ix) FEATURE:
    (A) NAME/KEY: misc_feature
    (B) LOCATION:29
    (D) OTHER INFORMATION:/note= "B = C or G or T"

(ix) FEATURE:
    (A) NAME/KEY: misc_feature
    (B) LOCATION:30
    (D) OTHER INFORMATION:/note= "N = A or C or G or T"

(ix) FEATURE:
    (A) NAME/KEY: misc_feature
    (B) LOCATION:31
    (D) OTHER INFORMATION:/note= "N = A or C or G or T"

(ix) FEATURE:
    (A) NAME/KEY: misc_feature
    (B) LOCATION:32
    (D) OTHER INFORMATION:/note= "B = C or G or T"

(ix) FEATURE:
    (A) NAME/KEY: misc_feature
    (B) LOCATION:33
    (D) OTHER INFORMATION:/note= "N = A or C or G or T"

(ix) FEATURE:
    (A) NAME/KEY: misc_feature
    (B) LOCATION:34
    (D) OTHER INFORMATION:/note= "N = A or C or G or T"

(ix) FEATURE:
    (A) NAME/KEY: misc_feature
    (B) LOCATION:35
    (D) OTHER INFORMATION:/note= "B = C or G or T"

(ix) FEATURE:
    (A) NAME/KEY: misc_feature
    (B) LOCATION:36
    (D) OTHER INFORMATION:/note= "N = A or C or G or T"

(ix) FEATURE:
    (A) NAME/KEY: misc_feature
    (B) LOCATION:39
    (D) OTHER INFORMATION:/note= "N = A or C or G or T"

```
        (ix) FEATURE:
              (A) NAME/KEY: misc_feature
              (B) LOCATION:40
              (D) OTHER INFORMATION:/note= "N = A or C or G or T"

(ix) FEATURE:
              (A) NAME/KEY: misc_feature
              (B) LOCATION:41
              (D) OTHER INFORMATION:/note= "B = C or G or T"

(ix) FEATURE:
              (A) NAME/KEY: misc_feature
              (B) LOCATION:42
              (D) OTHER INFORMATION:/note= "N = A or C or G or T"

(ix) FEATURE:
              (A) NAME/KEY: misc_feature
              (B) LOCATION:43
              (D) OTHER INFORMATION:/note= "N = A or C or G or T"

(ix) FEATURE:
              (A) NAME/KEY: misc_feature
              (B) LOCATION:44
              (D) OTHER INFORMATION:/note= "B = C or G or T"

(ix) FEATURE:
              (A) NAME/KEY: misc_feature
              (B) LOCATION:45
              (D) OTHER INFORMATION:/note= "N = A or C or G or T"

(ix) FEATURE:
              (A) NAME/KEY: misc_feature
              (B) LOCATION:46
              (D) OTHER INFORMATION:/note= "N = A or C or G or T"

(ix) FEATURE:
              (A) NAME/KEY: misc_feature
              (B) LOCATION:47
              (D) OTHER INFORMATION:/note= "B = C or G or T"

(ix) FEATURE:
              (A) NAME/KEY: misc_feature
              (B) LOCATION:48
              (D) OTHER INFORMATION:/note= "N = A or C or G or T"

(ix) FEATURE:
              (A) NAME/KEY: misc_feature
              (B) LOCATION:49
              (D) OTHER INFORMATION:/note= "N = A or C or G or T"

(ix) FEATURE:
              (A) NAME/KEY: misc_feature
              (B) LOCATION:50
              (D) OTHER INFORMATION:/note= "B = C or G or T"

(xi) SEQUENCE DESCRIPTION: SEQ ID NO: 11:

GGCTCTGATG GAAGACGTGC AGCNNBNNBN NBNNBNCTNN BNNBNNBNNB TGCTCCAGAG    60

TCTTCCTCCT GTCG                                                    74

(2) INFORMATION FOR SEQ ID NO: 12:

(i) SEQUENCE CHARACTERISTICS:
              (A) LENGTH: 74 base pairs
              (B) TYPE: nucleic acid
              (C) STRANDEDNESS: single
              (D) TOPOLOGY: linear (ii) MOLECULE TYPE: other nucleic acid
              (A) DESCRIPTION: /desc = "hypervariable DNA oligo"

(ix) FEATURE:
              (A) NAME/KEY: misc_feature
              (B) LOCATION:24
              (D) OTHER INFORMATION:/note= "N = A or C or G or T"
```

-continued

```
(ix) FEATURE:
    (A) NAME/KEY: misc_feature
    (B) LOCATION:25
    (D) OTHER INFORMATION:/note= "N = A or C or G or T"

(ix) FEATURE:
    (A) NAME/KEY: misc_feature
    (B) LOCATION:26
    (D) OTHER INFORMATION:/note= "B = C or G or T"

(ix) FEATURE:
    (A) NAME/KEY: misc_feature
    (B) LOCATION:27
    (D) OTHER INFORMATION:/note= "N = A or C or G or T"

(ix) FEATURE:
    (A) NAME/KEY: misc_feature
    (B) LOCATION:28
    (D) OTHER INFORMATION:/note= "N = A or C or G or T"

(ix) FEATURE:
    (A) NAME/KEY: misc_feature
    (B) LOCATION:29
    (D) OTHER INFORMATION:/note= "B = C or G or T"

(ix) FEATURE:
    (A) NAME/KEY: misc_feature
    (B) LOCATION:30
    (D) OTHER INFORMATION:/note= "N = A or C or G or T"

(ix) FEATURE:
    (A) NAME/KEY: misc_feature
    (B) LOCATION:31
    (D) OTHER INFORMATION:/note= "N = A or C or G or T"

(ix) FEATURE:
    (A) NAME/KEY: misc_feature
    (B) LOCATION:32
    (D) OTHER INFORMATION:/note= "B = C or G or T"

(ix) FEATURE:
    (A) NAME/KEY: misc_feature
    (B) LOCATION:33
    (D) OTHER INFORMATION:/note= "N = A or C or G or T"

(ix) FEATURE:
    (A) NAME/KEY: misc_feature
    (B) LOCATION:34
    (D) OTHER INFORMATION:/note= "N = A or C or G or T"

(ix) FEATURE:
    (A) NAME/KEY: misc_feature
    (B) LOCATION:35
    (D) OTHER INFORMATION:/note= "B = C or G or T"

(ix) FEATURE:
    (A) NAME/KEY: misc_feature
    (B) LOCATION:36
    (D) OTHER INFORMATION:/note= "N = A or C or G or T"

(ix) FEATURE:
    (A) NAME/KEY: misc_feature
    (B) LOCATION:38
    (D) OTHER INFORMATION:/note= "M = A or C"

(ix) FEATURE:
    (A) NAME/KEY: misc_feature
    (B) LOCATION:39
    (D) OTHER INFORMATION:/note= "N = A or C or G or T"

(ix) FEATURE:
    (A) NAME/KEY: misc_feature
    (B) LOCATION:40
    (D) OTHER INFORMATION:/note= "N = A or C or G or T"
```

(ix) FEATURE:
    (A) NAME/KEY: misc_feature
    (B) LOCATION:41
    (D) OTHER INFORMATION:/note= "B = C or G or T"

(ix) FEATURE:
    (A) NAME/KEY: misc_feature
    (B) LOCATION:42
    (D) OTHER INFORMATION:/note= "N = A or C or G or T"

(ix) FEATURE:
    (A) NAME/KEY: misc_feature
    (B) LOCATION:43
    (D) OTHER INFORMATION:/note= "N = A or C or G or T"

(ix) FEATURE:
    (A) NAME/KEY: misc_feature
    (B) LOCATION:44
    (D) OTHER INFORMATION:/note= "B = C or G or T"

(ix) FEATURE:
    (A) NAME/KEY: misc_feature
    (B) LOCATION:45
    (D) OTHER INFORMATION:/note= "N = A or C or G or T"

(ix) FEATURE:
    (A) NAME/KEY: misc_feature
    (B) LOCATION:46
    (D) OTHER INFORMATION:/note= "N = A or C or G or T"

(ix) FEATURE:
    (A) NAME/KEY: misc_feature
    (B) LOCATION:47
    (D) OTHER INFORMATION:/note= "B = C or G or T"

(ix) FEATURE:
    (A) NAME/KEY: misc_feature
    (B) LOCATION:48
    (D) OTHER INFORMATION:/note= "N = A or C or G or T"

(ix) FEATURE:
    (A) NAME/KEY: misc_feature
    (B) LOCATION:49
    (D) OTHER INFORMATION:/note= "N = A or C or G or T"

(ix) FEATURE:
    (A) NAME/KEY: misc_feature
    (B) LOCATION:50
    (D) OTHER INFORMATION:/note= "B = C or G or T"

(xi) SEQUENCE DESCRIPTION: SEQ ID NO: 12:

GGCTCTGATG GAAGACGTGC AGCNNBNNBN NBNNBNAMNN BNNBNNBNNB TGCTCCAGAG    60

TCTTCCTCCT GTCG                                                    74

(2) INFORMATION FOR SEQ ID NO: 13:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "hypervariable DNA oligo"

(ix) FEATURE:
        (A) NAME/KEY: misc_feature
        (B) LOCATION:24
        (D) OTHER INFORMATION:/note= "N = A or C or G or T"

(ix) FEATURE:
        (A) NAME/KEY: misc_feature
        (B) LOCATION:25
        (D) OTHER INFORMATION:/note= "N = A or C or G or T"

```
     (ix) FEATURE:
           (A) NAME/KEY: misc_feature
           (B) LOCATION:26
           (D) OTHER INFORMATION:/note= "B = C or G or T"

(ix) FEATURE:
           (A) NAME/KEY: misc_feature
           (B) LOCATION:27
           (D) OTHER INFORMATION:/note= "N = A or C or G or T"

(ix) FEATURE:
           (A) NAME/KEY: misc_feature
           (B) LOCATION:28
           (D) OTHER INFORMATION:/note= "N = A or C or G or T"

(ix) FEATURE:
           (A) NAME/KEY: misc_feature
           (B) LOCATION:29
           (D) OTHER INFORMATION:/note= "B = C or G or T"

(ix) FEATURE:
           (A) NAME/KEY: misc_feature
           (B) LOCATION:30
           (D) OTHER INFORMATION:/note= "N = A or C or G or T"

(ix) FEATURE:
           (A) NAME/KEY: misc_feature
           (B) LOCATION:31
           (D) OTHER INFORMATION:/note= "N = A or C or G or T"

(ix) FEATURE:
           (A) NAME/KEY: misc_feature
           (B) LOCATION:32
           (D) OTHER INFORMATION:/note= "B = C or G or T"

(ix) FEATURE:
           (A) NAME/KEY: misc_feature
           (B) LOCATION:33
           (D) OTHER INFORMATION:/note= "N = A or C or G or T"

(ix) FEATURE:
           (A) NAME/KEY: misc_feature
           (B) LOCATION:34
           (D) OTHER INFORMATION:/note= "N = A or C or G or T"

(ix) FEATURE:
           (A) NAME/KEY: misc_feature
           (B) LOCATION:35
           (D) OTHER INFORMATION:/note= "B = C or G or T"

(ix) FEATURE:
           (A) NAME/KEY: misc_feature
           (B) LOCATION:36
           (D) OTHER INFORMATION:/note= "N = A or C or G or T"

(ix) FEATURE:
           (A) NAME/KEY: misc_feature
           (B) LOCATION:38
           (D) OTHER INFORMATION:/note= "B = C or G or T"

(ix) FEATURE:
           (A) NAME/KEY: misc_feature
           (B) LOCATION:39
           (D) OTHER INFORMATION:/note= "N = A or C or G or T"

(ix) FEATURE:
           (A) NAME/KEY: misc_feature
           (B) LOCATION:40
           (D) OTHER INFORMATION:/note= "N = A or C or G or T"

(ix) FEATURE:
           (A) NAME/KEY: misc_feature
           (B) LOCATION:41
           (D) OTHER INFORMATION:/note= "B = C or G or T"

(ix) FEATURE:
           (A) NAME/KEY: misc_feature
           (B) LOCATION:42
           (D) OTHER INFORMATION:/note= "N = A or C or G or T"
```

```
        (ix) FEATURE:
              (A) NAME/KEY: misc_feature
              (B) LOCATION:43
              (D) OTHER INFORMATION:/note= "N = A or C or G or T"

(ix) FEATURE:
              (A) NAME/KEY: misc_feature
              (B) LOCATION:44
              (D) OTHER INFORMATION:/note= "B = C or G or T"

(ix) FEATURE:
              (A) NAME/KEY: misc_feature
              (B) LOCATION:45
              (D) OTHER INFORMATION:/note= "N = A or C or G or T"

(ix) FEATURE:
              (A) NAME/KEY: misc_feature
              (B) LOCATION:46
              (D) OTHER INFORMATION:/note= "N = A or C or G or T"

(ix) FEATURE:
              (A) NAME/KEY: misc_feature
              (B) LOCATION:47
              (D) OTHER INFORMATION:/note= "B = C or G or T"

(ix) FEATURE:
              (A) NAME/KEY: misc_feature
              (B) LOCATION:48
              (D) OTHER INFORMATION:/note= "N = A or C or G or T"

(ix) FEATURE:
              (A) NAME/KEY: misc_feature
              (B) LOCATION:49
              (D) OTHER INFORMATION:/note= "N = A or C or G or T"

(ix) FEATURE:
              (A) NAME/KEY: misc_feature
              (B) LOCATION:50
              (D) OTHER INFORMATION:/note= "B = C or G or T"

(xi) SEQUENCE DESCRIPTION: SEQ ID NO: 13:

GGCTCTGATG GAAGACGTGC AGCNNBNNBN NBNNBNTBNN BNNBNNBNNB TGCTCCAGAG      60

TCTTCCTCCT GTCG                                                      74

(2) INFORMATION FOR SEQ ID NO: 14:

(i) SEQUENCE CHARACTERISTICS:
              (A) LENGTH: 22 base pairs
              (B) TYPE: nucleic acid
              (C) STRANDEDNESS: single
              (D) TOPOLOGY: linear (ii) MOLECULE TYPE: other nucleic acid
              (A) DESCRIPTION: /desc = "DNA primer"

(xi) SEQUENCE DESCRIPTION: SEQ ID NO: 14:

GGCTCTGATG GAAGACGTGC AG                                             22

(2) INFORMATION FOR SEQ ID NO: 15:

(i) SEQUENCE CHARACTERISTICS:
              (A) LENGTH: 22 base pairs
              (B) TYPE: nucleic acid
              (C) STRANDEDNESS: single
              (D) TOPOLOGY: linear (ii) MOLECULE TYPE: other nucleic acid
              (A) DESCRIPTION: /desc = "DNA primer"

(xi) SEQUENCE DESCRIPTION: SEQ ID NO: 15:

CGACAGGAGG AAGACTCTGG AG                                             22
```

(2) INFORMATION FOR SEQ ID NO: 16:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA vector"

(xi) SEQUENCE DESCRIPTION: SEQ ID NO: 16:

```
GGCGAGCTCC CGTGCAGCGG TCTTCAGCGC TTGCCGTCTG ACCGTAGCGC TGGAAGACGC    60

TCCAGAGGGT ACCCCGATAT CAGAGCTGAA                                     90
```

(2) INFORMATION FOR SEQ ID NO: 17:

(i) SEQUENCE CHARACTERISTICS:
        (A) LENGTH: 4614 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 17:

```
GGCGAGCTCC CGTGCAGCGC TCCAGGTACC CCGATATCAG AGCTGAAACT GTTGAAAGTT    60

GTTTAGCAAA ATCCCATACA GAAAATTCAT TTACTAACGT CTGGAAAGAC GACAAAACTT   120

TAGATCGTTA CGCTAACTAT GAGGGCTGTC TGTGGAATGC TACAGGCGTT GTAGTTTGTA   180

CTGGTGACGA AACTCAGTGT TACGGTACAT GGGTTCCTAT TGGGCTTGCT ATCCCTGAAA   240

ATGAGGGTGG TGGCTCTGAG GGTGGCGGTT CTGAGGGTGG CGGTTCTGAG GGTGGCGGTA   300

CTAAACCTCC TGAGTACGGT GATACACCTA TTCCGGGCTA TACTTATATC AACCCTCTCG   360

ACGGCACTTA TCCGCCTGGT ACTGAGCAAA ACCCCGCTAA TCCTAATCCT TCTCTTGAGG   420

AGTCTCAGCC TCTTAATACT TTCATGTTTC AGAATAATAG GTTCCGAAAT AGGCAGGGGG   480

CATTAACTGT TTATACGGGC ACTGTTACTC AAGGCACTGA CCCCGTTAAA ACTTATTACC   540

AGTACACTCC TGTATCATCA AAAGCCATGT ATGACGCTTA CTGGAACGGT AAATTCAGAG   600

ACTGCGCTTT CCATTCTGGC TTTAATGAAG ATCCATTCGT TTGTGAATAT CAAGGCCAAT   660

CGTCTGACCT GCCTCAACCT CCTGTCAATG CTGGCGGCGG CTCTGGTGGT GGTTCTGGTG   720

GCGGCTCTGA GGGTGGTGGC TCTGAGGGTG GCGGTTCTGA GGGTGGCGGC TCTGAGGGAG   780

GCGGTTCCGG TGGTGGCTCT GGTTCCGGTG ATTTTGATTA TGAAAAGATG GCAAACGCTA   840

ATAAGGGGGC TATGACCGAA AATGCCGATG AAAACGCGCT ACAGTCTGAC GCTAAAGGCA   900

AACTTGATTC TGTCGCTACT GATTACGGTG CTGCTATCGA TGGTTTCATT GGTGACGTTT   960

CCGGCCTTGC TAATGGTAAT GGTGCTACTG GTGATTTTGC TGGCTCTAAT TCCCAAATGG  1020

CTCAAGTCGG TGACGGTGAT AATTCACCTT TAATGAATAA TTTCCGTCAA TATTTACCTT  1080

CCCTCCCTCA ATCGGTTGAA TGTCGCCCTT TTGTCTTTGG CGCTGGTAAA CCATATGAAT  1140

TTTCTATTGA TTGTGACAAA ATAAACTTAT TCCGTGGTGT CTTTGCGTTT CTTTTATATG  1200

TTGCCACCTT TATGTATGTA TTTTCTACGT TTGCTAACAT ACTGCGTAAT AAGGAGTCTT  1260

AATGACTCTA GAGGTCGAAA TTCACCTCGA AGCAAGCTG ATAAACCGAT ACAATTAAAG   1320

GCTCCTTTTG GAGCCTTTTT TTTTGGAGAT TTTCAACGTG AAAAAATTAT TATTCGCAAT  1380

TCCAAGCTAA TTCACCTCGA AGCAAGCTG ATAAACCGAT ACAATTAAAG GCTCCTTTTG   1440
```

-continued

```
GAGCCTTTTT TTTTGGAGAT TTTCAACGTG AAAAAATTAT TATTCGCAAT TCCAAGCTCT    1500
GCCTCGCGCG TTTCGGTGAT GACGGTGAAA ACCTCTGACA CATGCAGCTC CCGGAGACGG    1560
TCACAGCTTG TCTGTAAGCG GATGCAGATC ACGCGCCCTG TAGCGGCGCA TTAAGCGCGG    1620
CGGGTGTGGT GGTTACGCGC AGCGTGACCG CTACACTTGC CAGCGCCCTA GCGCCCGCTC    1680
CTTTCGCTTT CTTCCCTTCC TTTCTCGCCA CGTTCGCCAG CTTTCCCCGT CAAGCTCTAA    1740
ATCGGGGCT  CCCTTTAGGG TTCCGATTTA GTGCTTTACG GCACCTCGAC CCCAAAAAAC    1800
TTGATTAGGG TGATGGTTCA CGTAGTGGGC CATCGCCCTG ATAGACGGTT TTTCGCCCTT    1860
TGACGTTGGA GTCCACGTTC TTTAATAGTG GACTCTTGTT CCAAACTGGA ACAACACTCA    1920
ACCCTATCTC GGTCTATTCT TTTGATTTAT AAGGGATTTT GCCGATTTCG GCCTATTGGT    1980
TAAAAAATGA GCTGATTTAA CAAAAATTTA ACGCGAATTT TAACAAAATA TTAACGTTTA    2040
CAATTTGATC TGCGCTCGGT CGTTCGGCTG CGGCGAGCGG TATCAGCTCA CTCAAAGGCG    2100
GTAATACGGT TATCCACAGA ATCAGGGGAT AACGCAGGAA AGAACATGTG AGCAAAAGGC    2160
CAGCAAAAGG CCAGGAACCG TAAAAAGGCC GCGTTGCTGG CGTTTTTCCA TAGGCTCCGC    2220
CCCCCTGACG AGCATCACAA AAATCGACGC TCAAGTCAGA GGTGGCGAAA CCCGACAGGA    2280
CTATAAAGAT ACCAGGCGTT TCCCCCTGGA AGCTCCCTCG TGCGCTCTCC TGTTCCGACC    2340
CTGCCGCTTA CCGGATACCT GTCCGCCTTT CTCCCTTCGG GAAGCGTGGC GCTTTCTCAA    2400
TGCTCACGCT GTAGGTATCT CAGTTCGGTG TAGGTCGTTC GCTCCAAGCT GGGCTGTGTG    2460
CACGAACCCC CCGTTCAGCC CGACCGCTGC GCCTTATCCG GTAACTATCG TCTTGAGTCC    2520
AACCCGGTAA GACACGACTT ATCGCCACTG GCAGCAGCCA CTGGTAACAG GATTAGCAGA    2580
GCGAGGTATG TAGGCGGTGC TACAGAGTTC TTGAAGTGGT GGCCTAACTA CGGCTACACT    2640
AGAAGGACAG TATTTGGTAT CTGCGCTCTG CTGAAGCCAG TTACCTTCGG AAAAAGAGTT    2700
GGTAGCTCTT GATCCGGCAA ACAAACCACC GCTGGTAGCG GTGGTTTTTT TGTTTGCAAG    2760
CAGCAGATTA CGCGCAGAAA AAAAGGATCT CAAGAAGATC CTTTGATCTT TTCTACGGGG    2820
TCTGACGCTC AGTGGAACGA AAACTCACGT TAAGGGATTT TGGTCATGAG ATTATCAAAA    2880
AGGATCTTCA CCTAGATCCT TTTAAATTAA AAATGAAGTT TTAAATCAAT CTAAAGTATA    2940
TATGAGTAAA CTTGGTCTGA CAGTTACCAA TGCTTAATCA GTGAGGCACC TATCTCAGCG    3000
ATCTGTCTAT TTCGTTCATC CATAGTTGCC TGACTCCCCG TCGTGTAGAT AACTACGATA    3060
CGGGAGGGCT TACCATCTGG CCCCAGTGCT GCAATGATAC CGCGAGACCC ACGCTCACCG    3120
GCTCCGCTTT TATCAGCAAT AAACCAGCCA GCCGGAAGGG CCGAGCGCAG AAGTGGTCCT    3180
GCAACTTTAT CCGCCTCCAT CCAGTCTATT AATTGTTGCC GGGAAGCTAG AGTAAGTAGT    3240
TCGCCAGTTA ATAGTTTGCG CAACGTTGTT GCCATTGCTG CAGGCATCGT GGTGTCACGC    3300
TCGTCGTTTG GTATGGCTTC ATTCAGCTCC GGTTCCCAAC GATCAAGGCG AGTTACATGA    3360
TCCCCCATGT TGTGCAAAAA AGCGGTTAGC TCCTTCGGTC CTCCGATCGT TGTCAGAAGT    3420
AAGTTGGCCG CAGTGTTATC ACTCATGGTT ATGGCAGCAC TGCATAATTC TCTTACTGTC    3480
ATGCCATCCG TAAGATGCTT TTCTGTGACT GGTGAGTACT CAACCAAGTC ATTCTGAGAA    3540
TAGTGTATGC GGCGACCGAG TTGCTCTTGC CCGGCGTCAA CACGGGATAA TACCGCGCCA    3600
CATAGCAGAA CTTTAAAAGT GCTCATCATT GGAAAACGTT CTTCGGGGCG AAAACTCTCA    3660
AGGATCTTAC CGCTGTTGAG ATCCAGTTCG ATGTAACCCA CTCGTGCACC CAACTGATCT    3720
TCAGCATCTT TTACTTTCAC CAGCGTTTCT GGGTGAGCAA AAACAGGAAG GCAAAATGCC    3780
GCAAAAAAGG GAATAAGGGC GACACGGAAA TGTTGAATAC TCATACTCTT CCTTTTTCAA    3840
```

```
TATTATTGAA GCAGACAGTT TTATTGTTCA TGATGATATA TTTTTATCTT GTGCAATGTA      3900

ACATCAGAGA TTTTGAGACA CAACAGATCT GGCCATCATG ATGGAATGTT TCCCCGGTGG      3960

TGTTATCTGG CAGCAGTGCC GTCGATAGTA TGCAATTGAT AATTATTATC ATTTGCGGGT      4020

CCTTTCCGGC GATCCGCCTT GTTACGGGGC GGCGACCTCG CGGGTTTTCG CTATTTATGA      4080

AAATTTTCCG GTTTAAGGCG TTTCCGTTCT TCTTCGTCAT AACTTAATGT TTTTATTTAA      4140

AATACCCTCT GAAAAGAAAG GAAACGACAG GTGCTGAAAG CGAGCTTTTT GGCCACGATG      4200

CGTCCGGCGT AGAGGATCTC TCACCTACCA AACAATGCCC CCCTGCAAAA AATAAATTCA      4260

TATAAAAAAC ATACAGATAA CCATCTGCGG TGATAAATTA TCTCTGGCGG TGTTGACATA      4320

AATACCACTG GCGGTGATAC TGAGCACATC AGCAGGACGC ACTGACCACC ATGAAGGT        4380

CGCTCTTAAA ATTAAGCCCT GAAGAAGGGC AGCATTCAAA GCAGAAGGCT TTGGGGTGTG      4440

TGATACGAAA CGAAGCATTG GAATTCTACA ACTTGCTTGG ATTCCTACAA AGAAGCAGCA      4500

ATTTTCAGTG TCAGAAGTCG ACCAAGGAGG TCTAGATAAC GAGGGCAAAA AATGAAAAAG      4560

ACAGCTATCG CGATTGCAGT GGCACTGGCT GGTTTCGCTA CCGTAGCGCA GGCC           4614

(2) INFORMATION FOR SEQ ID NO: 18:

(i) SEQUENCE CHARACTERISTICS:
        (A) LENGTH: 4657 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 18:

GGCGAGCTCC CGTGCAGCGG TCTTCAGCGC TTGCCGTCTG ACCGTAGCGC TGGAAGACGC        60

TCCAGAGGGT ACCCCGATAT CAGAGCTGAA ACTGTTGAAA GTTGTTTAGC AAAATCCCAT       120

ACAGAAAATT CATTTACTAA CGTCTGGAAA GACGACAAAA CTTTAGATCG TTACGCTAAC       180

TATGAGGGCT GTCTGTGGAA TGCTACAGGC GTTGTAGTTT GTACTGGTGA CGAAACTCAG       240

TGTTACGGTA CATGGGTTCC TATTGGGCTT GCTATCCCTG AAAATGAGGG TGGTGGCTCT       300

GAGGGTGGCG GTTCTGAGGG TGGCGGTTCT GAGGGTGGCG GTACTAAACC TCCTGAGTAC       360

GGTGATACAC CTATTCCGGG CTATACTTAT ATCAACCCTC TCGACGGCAC TTATCCGCCT       420

GGTACTGAGC AAAACCCCGC TAATCCTAAT CCTTCTCTTG AGGAGTCTCA GCCTCTTAAT       480

ACTTTCATGT TTCAGAATAA TAGGTTCCGA AATAGGCAGG GGCATTAAC TGTTTATACG       540

GGCACTGTTA CTCAAGGCAC TGACCCCGTT AAAACTTATT ACCAGTACAC TCCTGTATCA       600

TCAAAAGCCA TGTATGACGC TTACTGGAAC GGTAAATTCA GAGACTGCGC TTTCCATTCT       660

GGCTTTAATG AAGATCCATT CGTTTGTGAA TATCAAGGCC AATCGTCTGA CCTGCCTCAA       720

CCTCCTGTCA ATGCTGGCGG CGGCTCTGGT GGTGGTTCTG GTGGCGGCTC TGAGGGTGGT       780

GGCTCTGAGG GTGGCGGTTC TGAGGGTGGC GGCTCTGAGG GAGGCGGTTC CGGTGGTGGC       840

TCTGGTTCCG GTGATTTTGA TTATGAAAAG ATGGCAAACG CTAATAAGGG GGCTATGACC       900

GAAAATGCCG ATGAAAACGC GCTACAGTCT GACGCTAAAG GCAAACTTGA TTCTGTCGCT       960

ACTGATTACG GTGCTGCTAT CGATGGTTTC ATTGGTGACG TTTCCGGCCT TGCTAATGGT      1020

AATGGTGCTA CTGGTGATTT TGCTGGCTCT AATTCCCAAA TGGCTCAAGT CGGTGACGTG      1080

GATAATTCAC CTTTAATGAA TAATTTCCGT CAATATTTAC CTTCCCTCCC TCAATCGGTT      1140

GAATGTCGCC CTTTTGTCTT TGGCGCTGGT AAACCATATG AATTTTCTAT TGATTGTGAC      1200
```

| | |
|---|---|
| AAAATAAACT TATTCCGTGG TGTCTTTGCG TTTCTTTTAT ATGTTGCCAC CTTTATGTAT | 1260 |
| GTATTTTCTA CGTTTGCTAA CATACTGCGT AATAAGGAGT CTTAATGACT CTAGAGGTCG | 1320 |
| AAATTCACCT CGAAAGCAAG CTGATAAACC GATACAATTA AAGGCTCCTT TTGGAGCCTT | 1380 |
| TTTTTTTGGA GATTTTCAAC GTGAAAAAAT TATTATTCGC AATTCCAAGC TAATTCACCT | 1440 |
| CGAAAGCAAG CTGATAAACC GATACAATTA AAGGCTCCTT TTGGAGCCTT TTTTTTTGGA | 1500 |
| GATTTTCAAC GTGAAAAAAT TATTATTCGC AATTCCAAGC TCTGCCTCGC GCGTTTCGGT | 1560 |
| GATGACGGTG AAAACCTCTG ACACATGCAG CTCCCGGAGA CGGTCACAGC TTGTCTGTAA | 1620 |
| GCGGATGCAG ATCACGCGCC CTGTAGCGGC GCATTAAGCG CGGCGGGTGT GGTGGTTACG | 1680 |
| CGCAGCGTGA CCGCTACACT TGCCAGCGCC CTAGCGCCCG CTCCTTTCGC TTTCTTCCCT | 1740 |
| TCCTTTCTCG CCACGTTCGC CAGCTTTCCC CGTCAAGCTC TAAATCGGGG GCTCCCTTTA | 1800 |
| GGGTTCCGAT TTAGTGCTTT ACGGCACCTC GACCCCAAAA AACTTGATTA GGGTGATGCT | 1860 |
| TCACGTAGTG GGCCATCGCC CTGATAGACG GTTTTTCGCC CTTTGACGTT GGAGTCCACG | 1920 |
| TTCTTTAATA GTGGACTCTT GTTCCAAACT GGAACAACAC TCAACCCTAT CTCGGTCTAT | 1980 |
| TCTTTTGATT TATAAGGGAT TTTGCCGATT TCGGCCTATT GGTTAAAAAA TGAGCTGATT | 2040 |
| TAACAAAAAT TTAACGCGAA TTTTAACAAA ATATTAACGT TTACAATTTG ATCTGCGCTC | 2100 |
| GGTCGTTCGG CTGCGGCGAG CGGTATCAGC TCACTCAAAG GCGGTAATAC GGTTATCCAC | 2160 |
| AGAATCAGGG GATAACGCAG GAAAGAACAT GTGAGCAAAA GGCCAGCAAA AGGCCAGGAA | 2220 |
| CCGTAAAAAG GCCGCGTTGC TGGCGTTTTT CCATAGGCTC CGCCCCCCTG ACGAGCATCA | 2280 |
| CAAAAATCGA CGCTCAAGTC AGAGGTGGCG AAACCCGACA GGACTATAAA GATACCAGGC | 2340 |
| GTTTCCCCCT GGAAGCTCCC TCGTGCGCTC TCCTGTTCCG ACCCTGCCGC TTACCGGATA | 2400 |
| CCTGTCCGCC TTTCTCCCTT CGGGAAGCGT GGCGCTTTCT CAATGCTCAC GCTGTAGGTA | 2460 |
| TCTCAGTTCG GTGTAGGTCG TTCGCTCCAA GCTGGGCTGT GTGCACGAAC CCCCCGTTCA | 2520 |
| GCCCGACCGC TGCGCCTTAT CCGGTAACTA TCGTCTTGAG TCCAACCCGG TAAGACACGA | 2580 |
| CTTATCGCCA CTGGCAGCAG CCACTGGTAA CAGGATTAGC AGAGCGAGGT ATGTAGGCGG | 2640 |
| TGCTACAGAG TTCTTGAAGT GGTGGCCTAA CTACGGCTAC ACTAGAAGGA CAGTATTTGG | 2700 |
| TATCTGCGCT CTGCTGAAGC CAGTTACCTT CGGAAAAAGA GTTGGTAGCT CTTGATCCGG | 2760 |
| CAAACAAACC ACCGCTGGTA GCGGTGGTTT TTTTGTTTGC AAGCAGCAGA TTACGCGCAG | 2820 |
| AAAAAAAGGA TCTCAAGAAG ATCCTTTGAT CTTTTCTACG GGGTCTGACG CTCAGTGGAA | 2880 |
| CGAAAACTCA CGTTAAGGGA TTTTGGTCAT GAGATTATCA AAAAGGATCT TCACCTAGAT | 2940 |
| CCTTTTAAAT TAAAAATGAA GTTTTAAATC AATCTAAAGT ATATATGAGT AAACTTGGTC | 3000 |
| TGACAGTTAC CAATGCTTAA TCAGTGAGGC ACCTATCTCA GCGATCTGTC TATTTCGTTC | 3060 |
| ATCCATAGTT GCCTGACTCC CCGTCGTGTA GATAACTACG ATACGGGAGG GCTTACCATC | 3120 |
| TGGCCCCAGT GCTGCAATGA TACCGCGAGA CCCACGCTCA CCGGCTCCGC TTTTATCAGC | 3180 |
| AATAAACCAG CCAGCCGGAA GGGCCGAGCG CAGAAGTGGT CCTGCAACTT TATCCGCCTC | 3240 |
| CATCCAGTCT ATTAATTGTT GCCGGGAAGC TAGAGTAAGT AGTTCGCCAG TTAATAGTTT | 3300 |
| GCGCAACGTT GTTGCCATTG CTGCAGGCAT CGTGGTGTCA CGCTCGTCGT TTGGTATGGC | 3360 |
| TTCATTCAGC TCCGGTTCCC AACGATCAAG GCGAGTTACA TGATCCCCCA TGTTGTGCAA | 3420 |
| AAAAGCGGTT AGCTCCTTCG GTCCTCCGAT CGTTGTCAGA AGTAAGTTGG CCGCAGTGTT | 3480 |
| ATCACTCATG GTTATGGCAG CACTGCATAA TTCTCTTACT GTCATGCCAT CCGTAAGATG | 3540 |

-continued

```
CTTTTCTGTG ACTGGTGAGT ACTCAACCAA GTCATTCTGA GAATAGTGTA TGCGGCGACC   3600

GAGTTGCTCT TGCCCGGCGT CAACACGGGA TAATACCGCG CCACATAGCA GAACTTTAAA   3660

AGTGCTCATC ATTGGAAAAC GTTCTTCGGG GCGAAAACTC TCAAGGATCT TACCGCTGTT   3720

GAGATCCAGT TCGATGTAAC CCACTCGTGC ACCCAACTGA TCTTCAGCAT CTTTTACTTT   3780

CACCAGCGTT TCTGGGTGAG CAAAAACAGG AAGGCAAAAT GCCGCAAAAA AGGGAATAAG   3840

GGCGACACGG AAATGTTGAA TACTCATACT CTTCCTTTTT CAATATTATT GAAGCAGACA   3900

GTTTTATTGT TCATGATGAT ATATTTTAT CTTGTGCAAT GTAACATCAG AGATTTTGAG    3960

ACACAACAGA TCTGGCCATC ATGATGGAAT GTTTCCCCGG TGGTGTTATC TGGCAGCAGT   4020

GCCGTCGATA GTATGCAATT GATAATTATT ATCATTTGCG GGTCCTTTCC GGCGATCCGC   4080

CTTGTTACGG GGCGGCGACC TCGCGGGTTT TCGCTATTTA TGAAAATTTT CCGGTTTAAG   4140

GCGTTTCCGT TCTTCTTCGT CATAAACTTAA TGTTTTTATT TAAAATACCC TCTGAAAAGA  4200

AAGGAAACGA CAGGTGCTGA AAGCGAGCTT TTTGGCCACG ATGCGTCCGG CGTAGAGGAT   4260

CTCTCACCTA CCAAACAATG CCCCCCTGCA AAAAATAAAT TCATATAAAA AACATACAGA   4320

TAACCATCTG CGGTGATAAA TTATCTCTGG CGGTGTTGAC ATAAATACCA CTGGCGGTGA   4380

TACTGAGCAC ATCAGCAGGA CGCACTGACC ACCATGAAGG TGACGCTCTT AAAATTAAGC   4440

CCTGAAGAAG GGCAGCATTC AAAGCAGAAG GCTTTGGGGT GTGTGATACG AAACGAAGCA   4500

TTGGAATTCT ACAACTTGCT TGGATTCCTA CAAAGAAGCA GCAATTTTCA GTGTCAGAAG   4560

TCGACCAAGG AGGTCTAGAT AACGAGGGCA AAAAATGAAA AAGACAGCTA TCGCGATTGC   4620

AGTGGCACTG GCTGGTTTCG CTACCGTAGC GCAGGCC                            4657
```